US012806450B2

(12) United States Patent
Shannon et al.

(10) Patent No.: US 12,806,450 B2
(45) Date of Patent: Nov. 24, 2026

(54) ARTICLE OF PERSONAL PROTECTIVE EQUIPMENT AND METHOD FOR USE WITH ARTICLE OF PERSONAL PROTECTIVE EQUIPMENT

(71) Applicant: 3M INNOVATIVE PROPERTIES COMPANY, St. Paul, MN (US)

(72) Inventors: Matthew Shannon, Salisbury, NC (US); Wesley M. Barbee, Oxboro, NC (US); Richard J. Sabacinski, Charlotte, NC (US)

(73) Assignee: SCOTT TECHNOLOGIES, INC., Monroe, NC (US)

( * ) Notice: Subject to any disclaimer, the term of this patent is extended or adjusted under 35 U.S.C. 154(b) by 212 days.

(21) Appl. No.: 18/562,614

(22) PCT Filed: May 20, 2022

(86) PCT No.: PCT/IB2022/054762
§ 371 (c)(1),
(2) Date: Nov. 20, 2023

(87) PCT Pub. No.: WO2022/249009
PCT Pub. Date: Dec. 1, 2022

(65) Prior Publication Data

US 2025/0010108 A1 Jan. 9, 2025

Related U.S. Application Data

(60) Provisional application No. 63/202,175, filed on May 28, 2021.

(51) Int. Cl.
*A62B 9/00* (2006.01)
*A42B 3/04* (2006.01)
(Continued)

(52) U.S. Cl.
CPC .......... *A62B 9/006* (2013.01); *F21V 33/0064* (2013.01); *G08B 21/04* (2013.01);
(Continued)

(58) Field of Classification Search
CPC .. G08B 21/04; G08B 21/043; G08B 21/0446; A61B 5/1116; A61B 5/1118;
(Continued)

(56) References Cited

U.S. PATENT DOCUMENTS 7,652,517 B2 1/2010 Corcelli
8,013,739 B2 9/2011 Parkulo et al.
(Continued)

FOREIGN PATENT DOCUMENTS

EP 2432380 7/2018
KR 20210131850 A * 11/2021 ........... A42B 3/0466
(Continued)

OTHER PUBLICATIONS

International Search Report for PCT International Application No. PCT/IB2022/054762, mailed on Aug. 30, 2022, 4 pages.
(Continued)

*Primary Examiner* — Sean P Dougherty
(74) *Attorney, Agent, or Firm* — Weisberg I.P. Law, P.A.

(57) ABSTRACT

The present disclosure provides an article of personal protective equipment (PPE). The article of PPE includes at least one sensor configured to generate motion signals indicative of a motion of a user of the article of PPE. The article of PPE further includes a controller configured to determine a plurality of motions of the user over a plurality of time periods. Each motion includes a corresponding magnitude and a corresponding direction over the corresponding time period. The controller is further configured to determine a motion pattern based on the plurality of motions, such that the motions pattern includes at least one motion from the
(Continued)

plurality of motions that has a non-zero value for the corresponding magnitude. The controller is further configured to determine an emergency event at least based on the motion pattern. The controller is further configured to generate an alert signal upon determination of the emergency event.

19 Claims, 16 Drawing Sheets

(51) Int. Cl.

| | |
|---|---|
| ***A61B 5/00*** | (2006.01) |
| ***A61B 5/11*** | (2006.01) |
| ***A62B 7/00*** | (2006.01) |
| ***A62B 18/02*** | (2006.01) |
| ***F21V 33/00*** | (2006.01) |
| ***G08B 21/04*** | (2006.01) |

(52) U.S. Cl.
CPC ........... *A42B 3/0406* (2013.01); *A42B 3/0433* (2013.01); *A42B 3/046* (2013.01); *A42B 3/0466* (2013.01); *A61B 5/1116* (2013.01); *A61B 5/1118* (2013.01); *A61B 5/4094* (2013.01); *A62B 7/00* (2013.01); *A62B 18/02* (2013.01)

(58) Field of Classification Search
CPC ......... A61B 5/4094; A62B 9/006; A62B 7/00; A62B 18/02; F21V 33/0064; A42B 3/0406; A42B 3/0433; A42B 3/0466
See application file for complete search history.

(56) References Cited

U.S. PATENT DOCUMENTS

| | | | |
|---|---|---|---|
| 10,542,332 | B2 | 1/2020 | Awiszus et al. |
| 2016/0354014 | A1 | 12/2016 | Lobner et al. |
| 2017/0347886 | A1 | 12/2017 | Tran |
| 2018/0342143 | A1 | 11/2018 | Kaplan et al. |
| 2020/0105116 | A1 | 4/2020 | Jang et al. |

FOREIGN PATENT DOCUMENTS

| | | | |
|---|---|---|---|
| WO | 2017062709 | A1 | 4/2017 |
| WO | 2019244125 | A2 | 12/2019 |
| WO | 2020075045 | A1 | 4/2020 |
| WO | 2020243061 | | 12/2020 |
| WO | 2021024185 | A1 | 2/2021 |

OTHER PUBLICATIONS

Product Manual: "3M™ Scott™ Air-Pak™ X3 Pro" A Product of 3M, 2018, 84 pages.

Schmid, "(In)visible Light Communication: Combining Illumination and Communication", SIGGRAPH 2014: 41st Annual Conference on Computer Graphics and Interactive Techniques, Aug. 2014, 2 pages.

Wilcox, "A Human Factors Perspective Auditory Alarm Signals" Biomedical Instrumentation & Technology Jul./Aug. 2011, vol. 45, No. 4, pp. 284-289.

* cited by examiner

ARTICLE OF PERSONAL PROTECTIVE EQUIPMENT AND METHOD FOR USE WITH ARTICLE OF PERSONAL PROTECTIVE EQUIPMENT

CROSS REFERENCE TO RELATED APPLICATIONS

This application is a national stage filing under 35 U.S.C. 371 of PCT/IB2022/054762, filed 20 May 2022, which claims the benefit of U.S. Provisional Patent Application No. 63/202,175, filed 28 May 2021, the disclosure of which is incorporated by reference in its/their entirety herein.

TECHNICAL FIELD

The present disclosure relates generally to an article of personal protective equipment and a method for use with the article of personal protective equipment.

BACKGROUND

A personal alert safety system (PASS) device, also known as a distress signal unit (DSU) or an automatic distress signal unit (ADSL), is a personal safety device that may be used by a user, such as an emergency services worker, to signal an emergency condition for the user. The PASS device is typically provided with an article of personal protective equipment (PPE), such as a self-contained breathing apparatus (SCBA), and is carried by the user in a hazardous area, for example, a burning building. The primary purpose of the PASS device is to generate an alarm when the user is in danger or distress. Conventionally, the PASS device receives input from sensors, such as accelerometers, to ascertain a state of motion of the user. When the PASS device determines that the user has been motionless for a predetermined period of time, for example 60 or 90 seconds, the PASS device generates the alarm.

SUMMARY

In a first aspect, the present disclosure provides an article of personal protective equipment (PPE). The article of PPE includes at least one sensor configured to generate motion signals indicative of a motion of a user of the article of PPE. The article of PPE further includes a controller communicably coupled with the at least one sensor. The controller is configured to determine a plurality of motions of the user over a plurality of time periods based on the motion signals received from the at least one sensor. Each motion from the plurality of motions occurs over a corresponding time period from the plurality of time periods. Each motion includes a corresponding magnitude and a corresponding direction over the corresponding time period. The controller is further configured to determine a motion pattern based on the plurality of motions, such that the motions pattern includes at least one motion from the plurality of motions that has a non-zero value for the corresponding magnitude. The controller is further configured to determine an emergency event at least based on the motion pattern. The controller is further configured to generate an alert signal upon determination of the emergency event.

In a second aspect, the present disclosure provides a method for use with an article of personal protective equipment (PPE). The article of PPE includes at least one sensor and a controller. The method includes generating, by the at least one sensor, motion signals indicative of a motion of a user of the article of PPE. The method further includes determining, by the controller, a plurality of motions of the user over a plurality of time periods based on the motion signals received from the at least one sensor. Each motion from the plurality of motions occurs over a corresponding time period from the plurality of time periods. Each motion includes a corresponding magnitude and a corresponding direction over the corresponding time period. The method further includes determining, by the controller, a motion pattern based on the plurality of motions, such that the motion pattern includes at least one motion from the plurality of motions that has a non-zero value for the corresponding magnitude. The method further includes determining, by the controller, an emergency event at least based on the motion pattern. The method further includes generating, the controller, an alert signal upon determination of the emergency event.

The details of one or more examples of the disclosure are set forth in the accompanying drawings and the description below. Other features, objects, and advantages of the disclosure will be apparent from the description and drawings, and from the claims.

BRIEF DESCRIPTION OF THE DRAWINGS

Exemplary embodiments disclosed herein is more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labelled with the same number.

DETAILED DESCRIPTION

Figure 1:
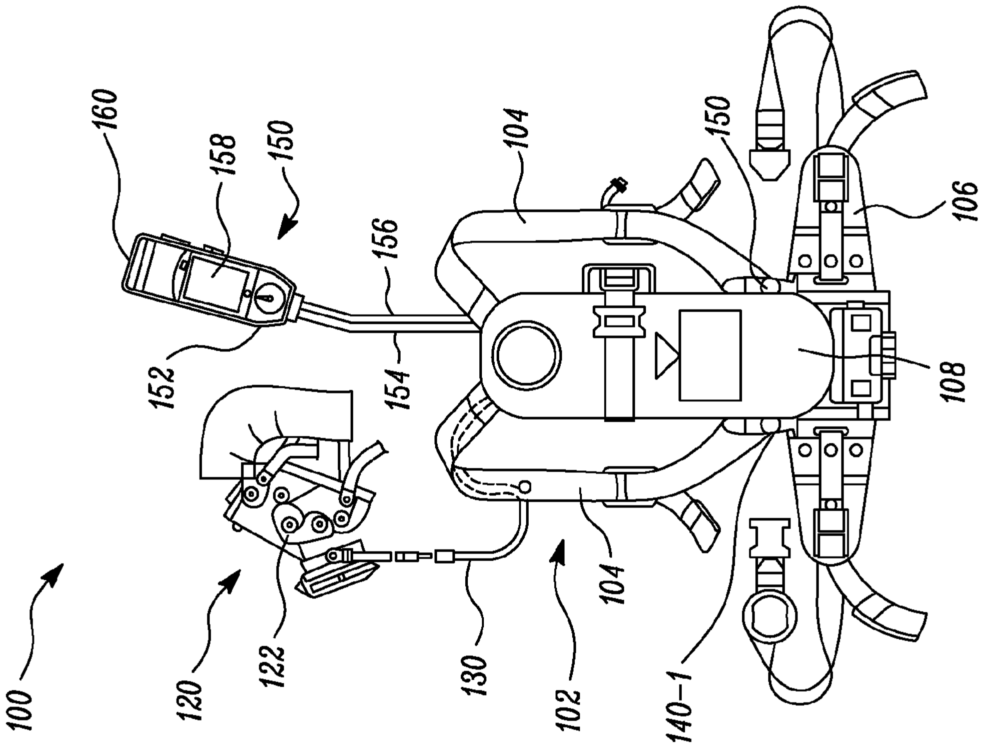
FIG. 1 is a schematic view of an article of personal protective equipment (PPE), according to an embodiment of the present disclosure.

In the following description, reference is made to the accompanying figures that form a part thereof and in which various embodiments are shown by way of illustration. It is to be understood that other embodiments are contemplated and is made without departing from the scope or spirit of the present disclosure. The following detailed description, therefore, is not to be taken in a limiting sense.

"Signal," as used herein, includes, but is not limited to, one or more electrical signals, optical signals, electromagnetic signals, analog and/or digital signals, one or more computer instructions, a bit and/or bit stream, or the like.

The present disclosure relates to an article of personal protective equipment (PPE) and a method for use with an article of PPE. The article of PPE may include a self-contained breathing apparatus (SCBA), a respirator, and the like.

Generally, an article of PPE may be provisioned with a personal alert safety system (PASS) device. The PASS device may be active when the article of PPE is used by a user in a hazardous environment, such as a burning building. The article of PPE may further include sensors, such as accelerometers, to determine a motion of the user. The PASS device is designed to ascertain a health or state of the user by monitoring the motion of the user. Conventionally, when the user is immobile for longer than a predetermined duration of time, such as 60 or 90 seconds, the PASS device registers an emergency event. The emergency event may correspond to any event that has immobilized the user in the hazardous environment. The PASS device may generate an alert upon registering the emergency event for the user. In conventional PASS devices, the alert is issued as an audio alert.

In some cases, however, the user of the article of PPE may face an emergency event even though the user is moving. The movement may be slow or intermittent due to impediments such as debris. For example, there may arise medical emergencies such as a seizure, which may be detected as movement by the conventional PASS device. Thus, there is an advantage in further analyzing motion of the user of the PPE in order to ascertain the state or health of the user.

Further, in some cases, the audio alert may not be clearly heard due to ambient noise. In some other cases, other users in the vicinity may be desensitized to the audio alert. In such cases, the audio alert may not be noticed, and the user may not receive the required assistance.

Further, in some other cases, the hazardous environment may be an environment in which the audio alert generated by the PASS device of the user bounces off other surfaces or echoes, which may result in the actual location of the user being obscured.

The present disclosure relates to an article of PPE. The article of PPE includes at least one sensor configured to generate motion signals indicative of a motion of a user of the article of PPE. The article of PPE further includes a controller communicably coupled with the at least one sensor. The controller is configured to determine a plurality of motions of the user over a plurality of time periods based on the motion signals received from the at least one sensor. Each motion from the plurality of motions occurs over a corresponding time period from the plurality of time periods. Each motion includes a corresponding magnitude and a corresponding direction over the corresponding time period. The controller is further configured to determine a motion pattern based on the plurality of motions, such that the motions pattern includes at least one motion from the plurality of motions that has a non-zero value for the corresponding magnitude. The controller is further configured to determine an emergency event at least based on the motion pattern. The controller is further configured to generate an alert signal upon determination of the emergency event.

The article of PPE of the present disclosure may analyze the motion of the user to determine motion patterns that may be indicative of emergency events for the user, such as medical conditions, entrapment, fall etc. Specifically, the article of PPE may determine emergency events for the user even though the user is in motion. The article of PPE may receive motion signals from an accelerometer that is provided on the user, and analyze the motion signals to determine a motion of the user over a period of time. The motion signals may include a magnitude and a direction of the motion. The article of PPE may determine a motion pattern from the motions of the user. The article of PPE may further be provided with a dataset of motion signatures corresponding to various emergency events for the user. Upon comparison of the determined motion pattern with the dataset, the emergency event for the user may be determined. For example, a motion pattern including a plurality of motions having a same magnitude and direction may be indicative of an emergency event corresponding to a medical condition, such as a seizure. In another example, a motion pattern including a plurality of motions, such that the motions have the same direction, but varying magnitudes, may be indicative of an emergency event where the user may be constrained, such as when trapped under debris. In a yet another example, a motion pattern including a plurality of motions with monotonically decreasing magnitudes may be indicative of an emergency event where the user may be fatigued. In yet another example, a motion pattern including a plurality of motions with monotonically increasing time periods may be indicative of an emergency event where the user may be losing consciousness. In a further example, a motion pattern including a single intense motion followed by a period of rest may be indicative of an emergency event where the user may have fallen or collapsed.

The article of PPE of the present disclosure further includes a plurality of light sources. When the PASS device registers an emergency event, a visual alert may be generated and transmitted through the plurality of light sources, in addition to the audio alert. The visual alert may draw further attention to the health or state of the user. In some cases, the visual alert, as well as the audio alert may carry embedded information, such as an identity of the user or a nature of the emergency event.

The article of PPE of the present disclosure may be provided with a detector to detect the audio alert generated by another user in a same environment. The article of PPE may determine a location of the other user based on an acoustic intensity and direction of the detected audio alert.

Further, the article of PPE may be provided with a model including a machine learning and an artificial intelligence to determine the emergency event.

Referring now to figures, FIG. 1 illustrates a schematic view of an article of personal protective equipment (PPE) 100 for a user (not shown), according to an embodiment of the present disclosure. The article of PPE 100 may interchangeably be referred to as "the article 100". In some examples, the user of the article 100 may be an emergency personnel, such as a firefighter. In some embodiments, the article 100 may include a breathing apparatus. In the illustrated embodiment of FIG. 1, the article 100 is a self-contained breathing apparatus (SCBA). In some other examples, the article 100 may include a respiratory protective equipment (RPS), a powered air purifying respirator (PAPR), a non-powered purifying respirator (APR), a self-retracting lifeline (SRL), or combinations thereof.

In some embodiments, the article 100 includes a backpack 102 including shoulder straps 104 and a belt 106, that is wearable by the user. The article 100 further includes an air cylinder 108 mounted on the backpack 102. The air cylinder 108 may include pressurized breathable air. The article 100 further includes a headgear 120 that may be worn on a head of the user. The headgear 120 may be used to provide protection to the head of the user. The headgear 120 may include a face mask, safety goggles, a safety hat, or combinations thereof. In the cases where the user is a firefighter, the article 100 may be worn by the user in a hazardous environment.

The headgear 120 may include a heads-up display (HUD) 122. The HUD 122 may display one or more parameters to the user of the article 100. The one or more parameters may include parameters associated with operation of the article 100, parameters associated with an environment in which the user is present, and a combination thereof. In some embodiments, the parameters associated with operation of the article 100 may include a remaining level of air in the air cylinder 108, a battery level of a battery pack (not shown) of the article 100, and the like. In some embodiments, the parameters associated with the environment in which the user is present may include a temperature of the environment, a level of smoke or dust in the environment, a level of any gases in the environment, a location of other emergency personnel in the environment, and the like. In some embodiments, the HUD 122 may further display a notification 542 (shown in FIG. 5C) containing instructions or information received from a command gateway (not shown), and/or from other portable devices (not shown). Specifically, the remaining level of air in the air cylinder 108 may be ascertained via a pressure sensor (not shown) located at an outlet pathway of the air cylinder 108.

The headgear 120 may further include a hearing device (not shown). In some examples, the hearing device may include a wired/wireless headphone and/or earphone. In some other examples, the hearing device may include a hearing protection device, such as, a pair of earmuffs.

The article 100 includes at least one sensor 140-1. The at least one sensor 140-1 may be disposed on the article 100. In some embodiments, the at least one sensor 140-1 includes at least one of an accelerometer, and a gyroscope. In some embodiments, the article 100 may include a plurality of sensors (including the at least one sensor 140-1) 140-1, 140-2 . . . 140-N (shown in FIG. 2). The plurality of sensors 140-1, 140-2 . . . 140-N may collectively be referred to as "the sensors 140", and may individually be referred to as "the sensor 140". In the illustrated embodiment of FIG. 1, the at least one sensor 140-1 is disposed at a base of the air cylinder 108, on the belt 106. In some embodiments, however, one or more of the sensors 140 may be disposed at different areas, for example, on the user. In some embodiments, the at least one sensor 140-1 may be arranged to determine a motion of the user of the article 100. The at least one sensor 140-1 is configured to generate motion signals 250 (shown in FIG. 2) indicative of the motion of the user of the article 100.

The article 100 further includes a personal alert safety system (PASS) device 150. The PASS device 150 may include a PASS control console 152. The PASS control console 152 may hang from an end of a pressure data line 154, connected via a pressure reducer (not shown) to the air cylinder 108, and a reinforced cable sheath 156. The article 100 may further include a personal digital assistance (PDA) device 158. The PDA device 158 may be located on the PASS device 150. In the illustrated embodiment of FIG. 1, the PASS device 150 is shown to be distributed at two locations on the article 100—at an end of the reinforced cable sheath 156, and at a base of the air cylinder 108, on the belt 106. In some embodiments, the reinforced cable sheath 156 carries electronic cables that connect the PASS control console 152 with the sensors 140 and the PASS device 150.

The article 100 may further include a plurality of light sources 524 (depicted in FIG. 5B) configured to emit light. In some embodiments, the plurality of light sources 524 may be disposed on the PASS device 150. In some embodiments, some of the plurality of light sources 524 may be disposed on the PASS device 150.

In some embodiments, the article 100 may further include a detector 160. The detector 160 may be any one of a microphone, a video camera, and a bone conduction device (not shown in figures). In the illustrated embodiment of FIG. 1, the detector 160 is disposed on the PASS device 150. However, in some embodiments, the detector 160 may be disposed proximal to the headgear 120. In some other embodiments, the detector 160 may be disposed on the headgear 120.

In some embodiments, the article 100 may include an air line/data line 130, which supplies air from the air cylinder 108 to the headgear 120 (e.g., a face mask) of the user, and provides data communications and power supply to the HUD 122.

Figure 2:
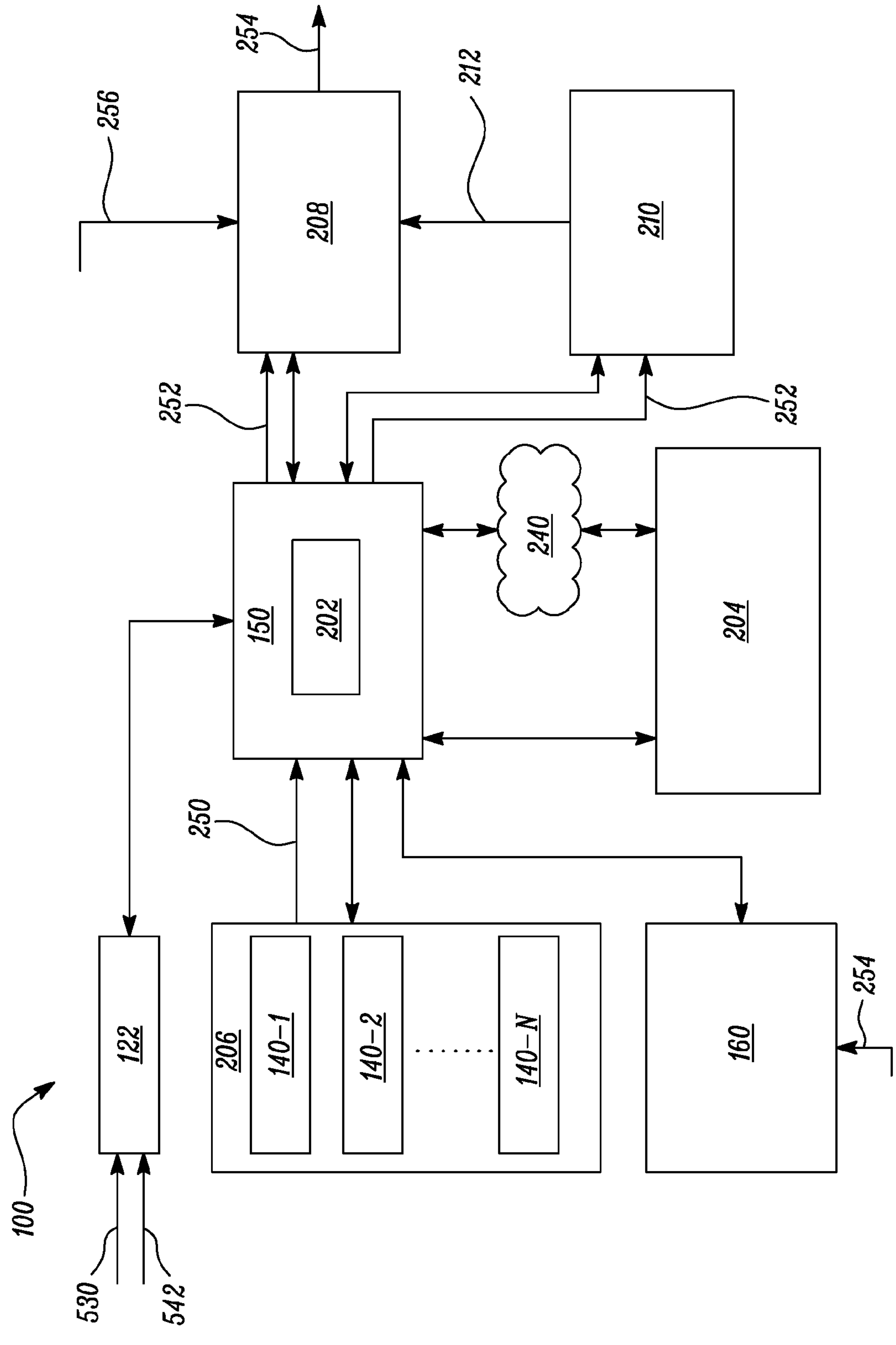
FIG. 2 is a schematic block diagram of the article of PPE, according to an embodiment of the present disclosure.

FIG. 2 illustrates a schematic block diagram of the article of PPE 100, according to an embodiment of the present disclosure.

Referring now to FIGS. 1 and 2, the article 100 includes a controller 202. In some embodiments, the PASS device 150 may include the controller 202. In some embodiments, the controller 202 may include a processor (not shown) and a memory (not shown) storing executable instructions. The processor may execute the instructions stored in the memory to implement a method or an algorithm.

In some embodiments, the article 100 includes a sensor module 206. The sensor module 206 is communicably coupled to the at least one sensor 140-1. In some embodiments, the sensor module is communicably coupled with the plurality of sensors 140. Further, the sensor module 206 is communicably coupled with the controller 202. Thus, controller 202 receives the motion signals 250 from the sensors 140, from the sensor module 206.

In some embodiments, the PASS device 150 is communicably coupled to the at least one sensor 140-1. Specifically, the controller 202 is communicably coupled to the at least one sensor 140-1. In some embodiments, the controller 202 of the PASS device 150 determines an emergency event for the user based on the motion signals 250 received from the at least one sensor 140-1. In some embodiments, the controller 202 of the PASS device 150 determines the emergency event for the user based on the motion signals 250 received from the sensors 140. In some embodiments, the controller 202 of the PASS device 150 may generate an alert signal 252 to register the emergency event for the user of the article 100. In some embodiments, the article 100 generates an alert 254 in response to the generated alert signal 252. In some embodiments, the PASS device 150 may be communicably coupled with the HUD 122 and the hearing device. The PASS device 150 may transmit the alert 254 to the hearing device in the form of an audio alert 510 (shown in FIG. 5A). In some embodiments, the audio alert 510 may be a sound with high frequency and high acoustic intensity. In some embodiments, the PASS device 150 may further transmit the alert 254 to the HUD 122 in the form of a visual alert 530 (shown in FIG. 5B) and the notification 542. In some embodiments, the article 100 may generate a haptic alert 212.

In some embodiments, the controller 202 is communicably coupled to the detector 160. In some embodiments, the detector 160 may be arranged to detect the alert 254 generated. The detector 160 may be configured to detect one or more of the audio alert 510, the visual alert 530, and the haptic alert 212.

In some embodiments, the article 100 further includes a memory 204 communicably coupled to the controller 202. In some embodiments, the memory 204 may be disposed in the article 100. In some embodiments, the memory 204 may be disposed in the PASS device 150 of the article 100. However, in some embodiments, the memory 204 may be located remotely. In such cases, the memory 204 is communicably coupled to the controller 202 through a network 240. Further, in some cases, the memory 204 may be a centralized memory and may be communicably coupled to controllers of a plurality of articles of PPE (not shown). In some embodiments, the memory 204 may store the executable instructions executable by the processor to implement the method or the algorithm.

Figure 3A:
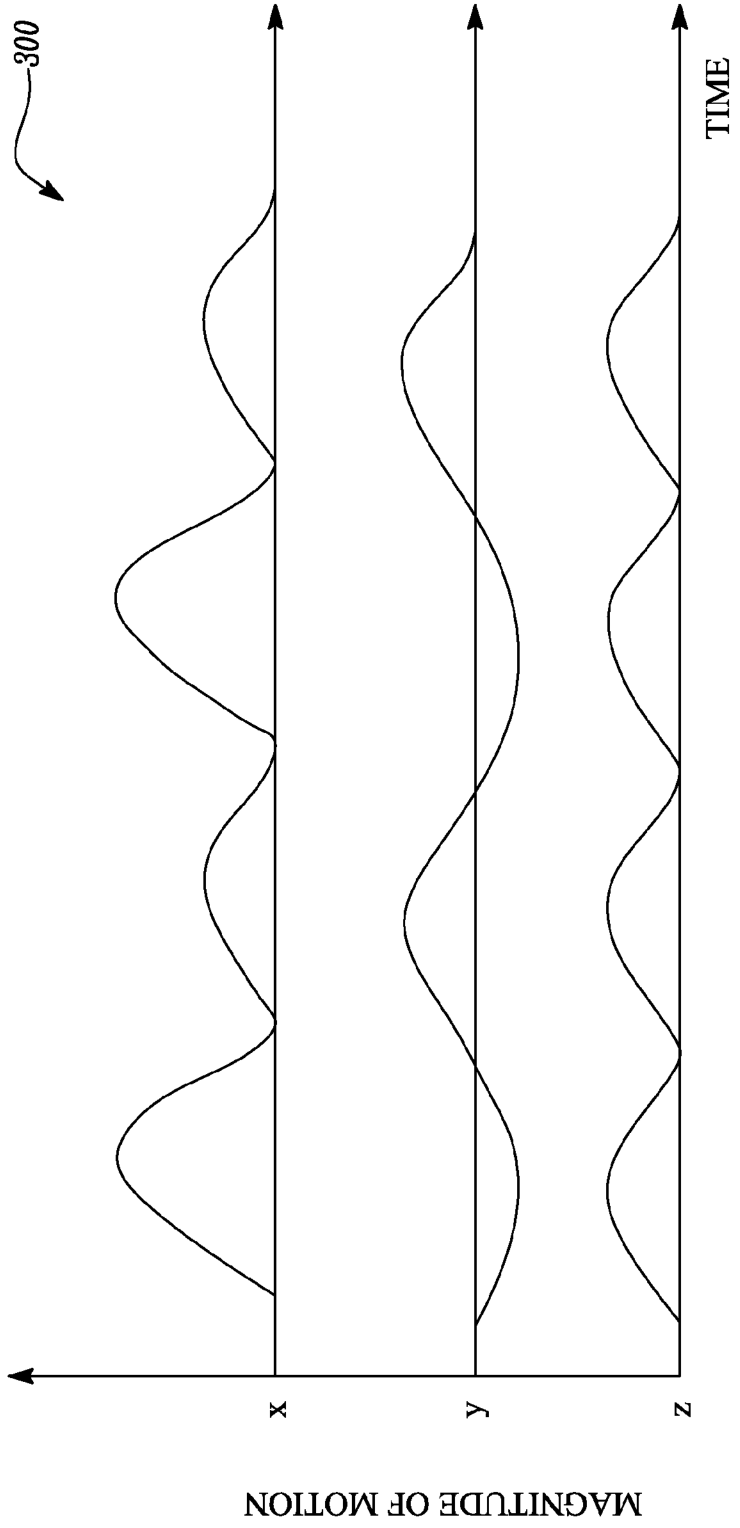
FIG. 3A is a plot depicting an example of motion signals received from an accelerometer.

FIG. 3A illustrates a plot 300 depicting an example of motion signals received from an accelerometer. There are many kinds of accelerometers available, which can detect motion signals indicative of different kinds of motion. In general, accelerometers measure force in one or more directions. In some cases, accelerometers measure force in three directions, namely, an x-axis, a y-axis, and a z-axis. From the measured force, acceleration, velocity, and position data may be determined. For example, a position of the accelerometer may be determined based on an axis along which gravitation force is measured.

Some other accelerometers may provide motions signals indicative of acceleration. Acceleration may include force corresponding to each of the three axes measured over a time period. It would be appreciated that, typically, accelerometers measure force, and that from the measured force, acceleration values are be determined. However, as used herein, the terms "acceleration" and "force" are interchangeable, and refer to a magnitude of motion. The plot 300 depicts magnitudes of motions along the x, y, and z-axes, as measured by the accelerometer along the ordinate, and time periods of magnitudes of motion along the abscissa. The motion along the three axes may be added vectorially to determine a resultant magnitude and direction of motion at any given time instant.

With reference to FIGS. 1, 2 and 3A, in some embodiments, the motion signals 250 include motion signals from an accelerometer.

Figure 3B:
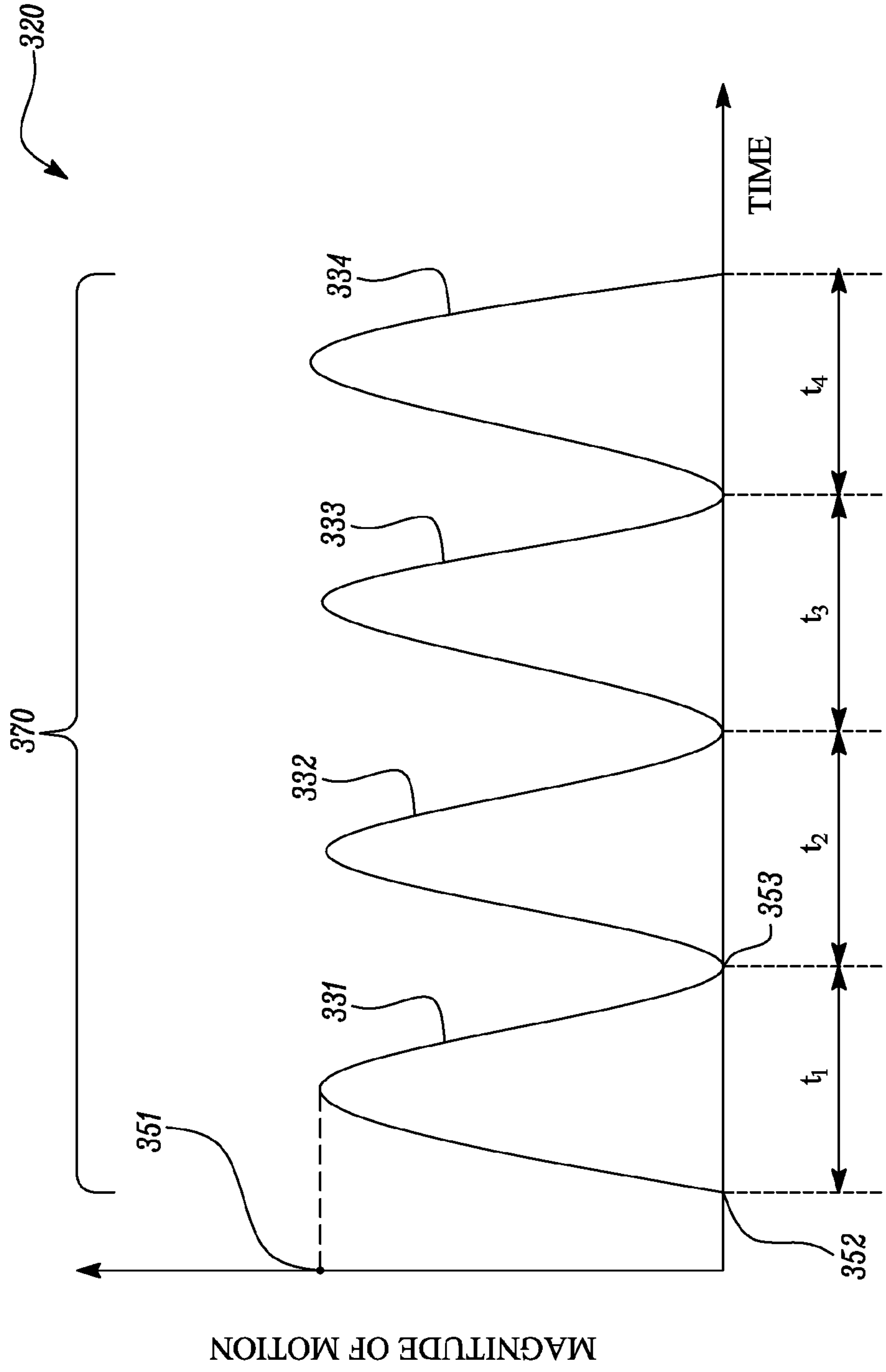
FIG. 3B is a plot depicting another example of motion signals received from an accelerometer.

FIG. 3B illustrates a plot 320 depicting another example of motion signals received from an accelerometer. Specifically, the plot 320 depicts magnitude of motion along any one direction (e.g., x-axis). The plot 320 depicts the magnitudes of motions along the ordinate axis, and time periods along the abscissa. The plot 320 further defines motions 331, 332, 333, 334 during corresponding time periods t1, t2, t3, t4. Typically, time periods are defined with respect to a sampling interval of the accelerometer.

In some embodiments, a motion may be defined with respect to a peak value of magnitude, disposed between a first minimum value of magnitude preceding the peak, and a second minimum value of magnitude succeeding the peak. Further, a time period may be defined as a period of time during which a motion occurs, and may be measured as time duration between occurrences of the first and second minimum values of the magnitude of motions.

In some embodiments, the first and second minimum values of magnitude may be approximately zero. A magnitude of motion may be defined with respect to the peak value of magnitude of the respective motion. In some embodiments, a motion may be said to have a non-zero value of magnitude when the peak value of magnitude of the motion is substantially higher than the first and second minimum values of magnitude. In some examples, the motion may have a non-zero value of magnitude when the peak value of magnitude of the motion is higher than the first and second minimum values of magnitude by a factor of 10, a factor of 100, a factor of 1000 etc. In embodiments of the present disclosure, a motion with non-zero value of magnitude may indicate a motion of the user of the article 100.

Similarly, a motion may be said to have a zero value of magnitude when the peak value of magnitude of motion is comparable to the first and second minimum value of magnitude. In some examples, the motion may be said to have a zero value of magnitude when the peak value of magnitude of the motion is less than 10 times that of the first and second minimum value of magnitude. In embodiments of the present disclosure, a motion with zero value of magnitude may indicate a resting state of the user of the article 100.

For example, the motion 331 is defined over time period t1. The motion 331 includes a peak 351, a first minimum 352 preceding the peak 351, and a second minimum 353 succeeding the peak 351. The time period t1 is defined as a time between the first and second minima 352, 353.

Referring now to FIGS. 1, 2, 3A and 3B, the controller 202 is configured to determine a plurality of motions (e.g., the motions 331, 332, 333, 334) of the user over a plurality of time periods (e.g., t1, t2, t3, t4, respectively) based on the motion signals 250 received from the at least one sensor 140-1. Each motion from the plurality of motions occurs over a corresponding time period from the plurality of time periods. Each motion includes a corresponding magnitude and a corresponding direction over the corresponding time period. In other words, the controller 202 is configured to determine motions 331, 332, 333, 334 of the user over respective time periods t1, t2, t3, t4, where the motions 331, 332, 333, 334 include the corresponding magnitudes and corresponding directions over the corresponding time periods t1, t2, t3, t4.

The controller 202 is further configured to determine a motion pattern based on the plurality of motions, such that the motion pattern includes at least one motion from the plurality of motions that has a non-zero value for the corresponding magnitude. In other words, the controller 202 determines that there is a motion pattern from the plurality of motions when at least one motion from the plurality of motions included in the motion pattern has a non-zero value of magnitude. Referring to FIG. 3B, a motion pattern 370 is determined by the controller 202. The motion pattern 370 includes the motions 331, 332, 333, 334, where the motions 331, 332, 333, 334 have non-zero values of magnitude.

The controller 202 is further configured to determine an emergency event at least based on the motion pattern 370. Subsequently, the controller 202 is configured to generate the alert signal 252 upon determination of the emergency event.

Figure 4:
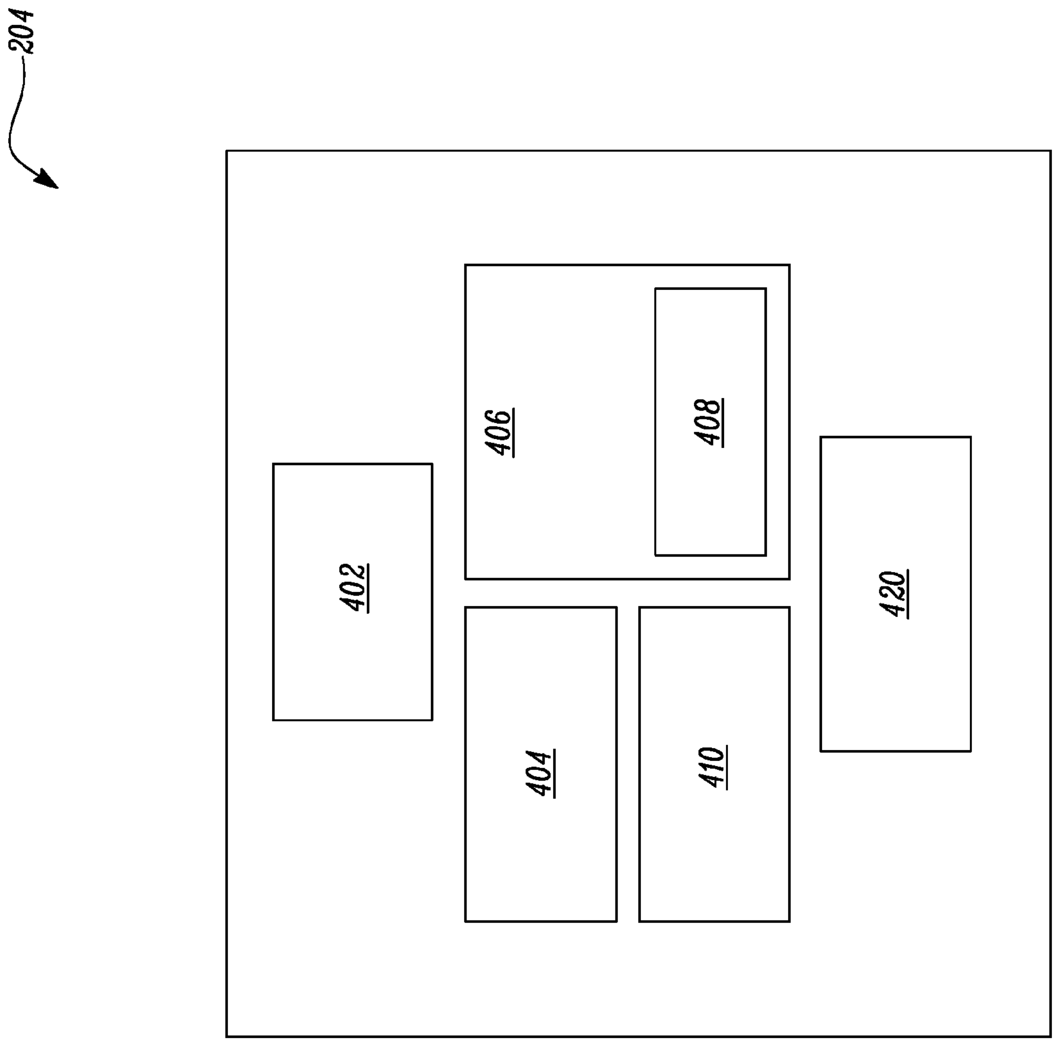
FIG. 4 is a schematic block diagram of a memory of the article of PPE of FIG. 2, according to an embodiment of the present disclosure.

FIG. 4 illustrates a schematic block diagram of the memory 204 of the article 100, according to an embodiment of the present disclosure. In some embodiments, the memory 204 stores a plurality of motion signatures. Specifically, the memory 204 may store a first dataset 402 including the plurality of motion signatures. In some embodiments, the plurality of motion signatures may correspond to a plurality of emergency events for the user of the article 100.

Referring now to FIGS. 1, 2, 3A, 3B and 4, the controller 202 is configured to determine the emergency event further based on a comparison between the motion pattern (e.g., the motion pattern 370) and the plurality of motion signatures.

In some embodiments, the article 100 further includes an alarm circuit 208 communicably coupled with the controller 202. The alarm circuit 208 is configured to generate the alert 254 upon receiving the alert signal 252 from the controller 202.

In some embodiments, the alert 254 includes an information 256 indicative of at least one of an identification of the user of the article 100 and a type of the emergency event. In some embodiments, the information 256 may be received by the alarm circuit 208 from the memory 204. The alarm circuit 208 may embed the information 256 in the alert 254.

An example of the emergency event may be a medical event such as a seizure. Another example of the emergency event may be a constraint event such as entrapment. Another example of the emergency event may be a fall event or a collapse event.

Referring FIGS. 1 and 2, in some embodiments, the article 100 may include a haptic device 210 communicably coupled to the alarm circuit 208 and to the controller 202. The haptic device 210 may be configured to generate the haptic alert 212 in response to the alert signal 252, such that the alert 254 includes the haptic alert 212.

In some embodiments, the memory 204 may include a second dataset 404 including the information 256 pertaining to identification of the user of the article 100. In cases where the memory 204 is a centralized memory, the second dataset 404 may include information pertaining to identification of users corresponding to the plurality of articles of PPE.

In some embodiments, the memory 204 may include a third dataset 406 including the information 256 pertaining to types of emergency events. In some embodiments, the types of emergency events may be based on motion patterns. In some embodiments, the third dataset 406 may include information pertaining to types of emergency events based on a historical data 408 of emergency events and associated motion patterns.

In some embodiments, the memory 204 may include a model 410. The model 410 may be a set of executable instructions executable by the controller 202 to determine the emergency event based on determined motion patterns. The model 410 utilizes detection techniques such as artificial intelligence for detecting emergency events based on the motion pattern.

In some embodiments, the model 410 may store at least a portion of motion signals 250 for determining the emergency event for the user of the article 100. In some embodiments, the model 410 may be trained based on usage data generated prior to receiving the motion signals 250. The usage data may include a plurality of emergency events and corresponding motion patterns. The emergency events and corresponding motion patterns may correspond to any one user of the article 100, or may be generic.

In some embodiments, the model 410 may be trained based on the historical data 408. In some embodiments, the model 410 may be based on machine learning and artificial intelligence.

In some embodiments, the memory 204 may include a fourth dataset 420 including other information such as details of an environment (e.g., an environment 600 of FIG. 6A) that the article 100 is present in.

Figure 5A:
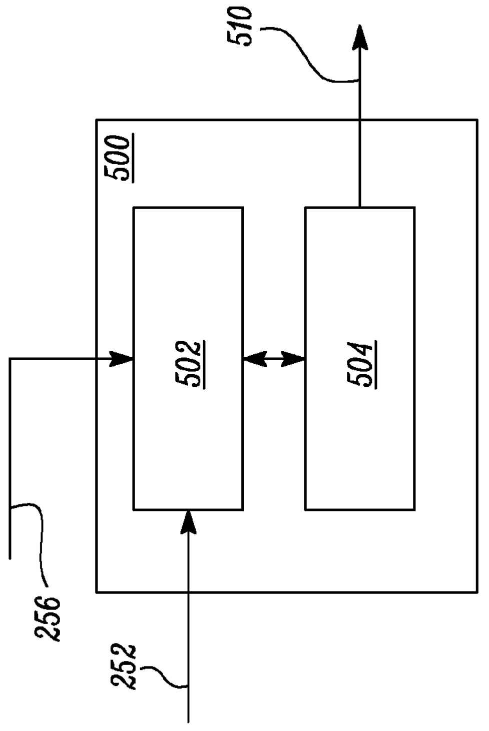
FIG. 5A is a schematic block diagram of an audio alarm generator of the article of PPE of FIG. 2, according to an embodiment of the present disclosure.

FIG. 5A illustrates a schematic block diagram of an audio alarm generator 500, according to an embodiment of the present disclosure. In some embodiments, the article 100 may include the audio alarm generator 500. The article 100 audio may further include an audio alarm circuit 502, and an audio alarm device 504. The audio alarm circuit 502 may be communicably coupled to the audio alarm device 504. The audio alarm device 504 may be operable by the audio alarm circuit 502.

Referring to FIGS. 1, 2, and 5A, the audio alarm generator 500 may be communicably coupled to the controller 202. Specifically, the audio alarm circuit 502 may be communicably coupled to the controller 202. In such cases, the audio alarm circuit 502 may receive the alert signal 252 from the controller 202. The audio alarm circuit 502 may then control the audio alarm device 504 to generate an audio alert 510.

In some embodiments, the audio alert 510 may include the information 256 indicative of at least one of the identification of the user of the article 100, and the type of the emergency event. In some embodiments, the audio alarm circuit 502 may receive the information 256, and embed the information 256 in the audio alert 510, such that the audio alert 510 includes the information 256.

In some embodiments, the audio alarm generator 500 may be communicably coupled to the alarm circuit 208. The alarm circuit 208 may receive the audio alert 510, and may generate the alert 254, such that the alert 254 includes the audio alert 510.

Figure 5B:
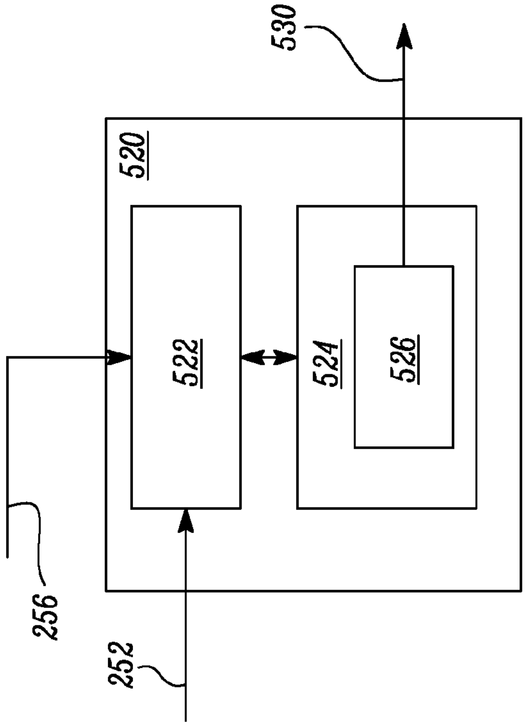
FIG. 5B is a schematic block diagram of a visual alarm generator of the article of PPE of FIG. 2, according to an embodiment of the present disclosure.

FIG. 5B illustrates a schematic block diagram of a visual alarm generator 520, according to an embodiment of the present disclosure. In some embodiments, the article 100 may include the visual alarm generator 520. The article 100 further includes the plurality of light sources 524, and a visual alarm circuit 522. The visual alarm circuit 522 is communicably coupled to the plurality of light sources 524. The plurality of light sources 524 may be operable by the visual alarm circuit 522. In some embodiments, each of the plurality of light sources 524 incudes a light emitting diode (LED).

Referring to FIGS. 1, 2, and 5B, the visual alarm generator 520 is communicably coupled to the controller 202. Specifically, the visual alarm circuit 522 is communicably coupled to the controller 202. In such cases, the visual alarm circuit 522 is configured to receive the alert signal 252 from the controller 202. The visual alarm circuit 522 is configured to control at least one optical parameter of each of the plurality of light sources 524 based on the alert signal 252 in order to generate the visual alert 530. In some embodiments, the at least one optical parameter includes one or more of a flicker rate, an optical intensity, a wavelength, and a switching pattern of the plurality of light sources 524.

In some embodiments, the visual alert 530 includes the information 256 indicative of at least one of the identification of the user of the article 100, and the type of the emergency event. The visual alarm circuit 522 may receive the information 256, and embed the information 256 in the visual alert 530, such that the visual alert 530 includes the information 256.

In some embodiments, the visual alarm generator 520 may be communicably coupled to the alarm circuit 208. The alarm circuit 208 may receive the visual alert 530, and may generate the alert 254, such that the alert 254 includes the visual alert 530.

Figure 5C:
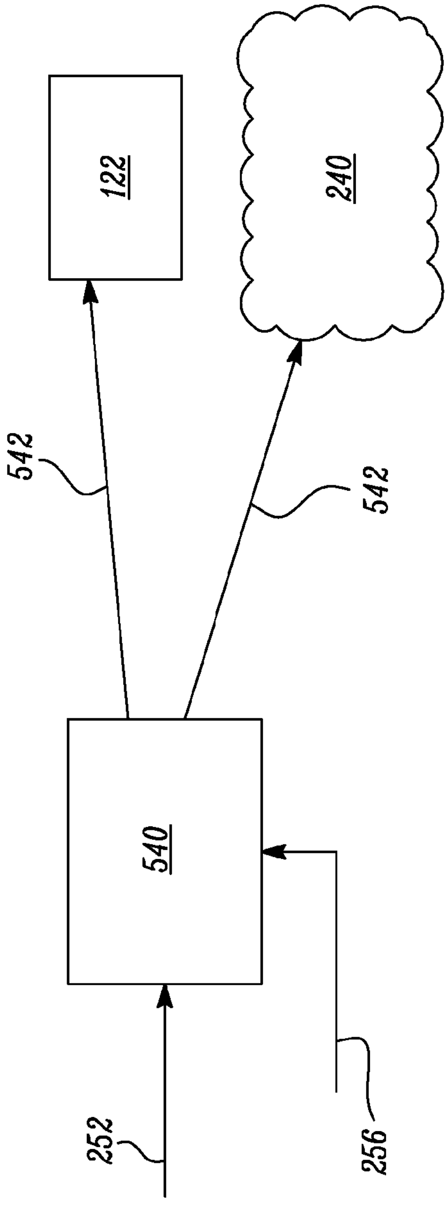
FIG. 5C is a schematic block diagram of a notification generator of the article of PPE of FIG. 2, according to an embodiment of the present disclosure.

FIG. 5C illustrates a schematic block diagram of a notification generator 540, according to an embodiment of the present disclosure. In some embodiments, the article 100 may include the notification generator 540.

Referring to FIGS. 1, 2, 5C, in some embodiments, the notification generator 540 may be communicably coupled with a network (e.g., the network 240). In some embodiments, the notification generator 540 may be communicably coupled to the controller 202. In some embodiments, the notification generator 540 receives the alert signal 252 from the controller 202. The notification generator 540 generates a notification 542 upon receiving the alert signal 252 from the controller 202. In some embodiments, the notification 542 includes the information 256 indicative of at least one of the identification of the user of the article 100, and the type of the emergency event. The notification generator 540 may transmit the notification 542 to the HUD 122 of the user of the article 100 and/or to the network 240. The notification generator 540 may receive the information 256, and embed the information 256 in the notification 542. In some embodiments, the notification generator 540 may be communicably coupled to the alarm circuit 208. The alarm circuit 208 may receive the notification 542, and may generate the alert 254, such that the alert 254 includes the notification 542.

Referring to FIGS. 2, 5A, 5B and 5C, therefore, in some embodiments, the alert 254 includes at least one of the audio alert 510, the visual alert 530, the haptic alert 212, and the notification 542.

Figure 6A:
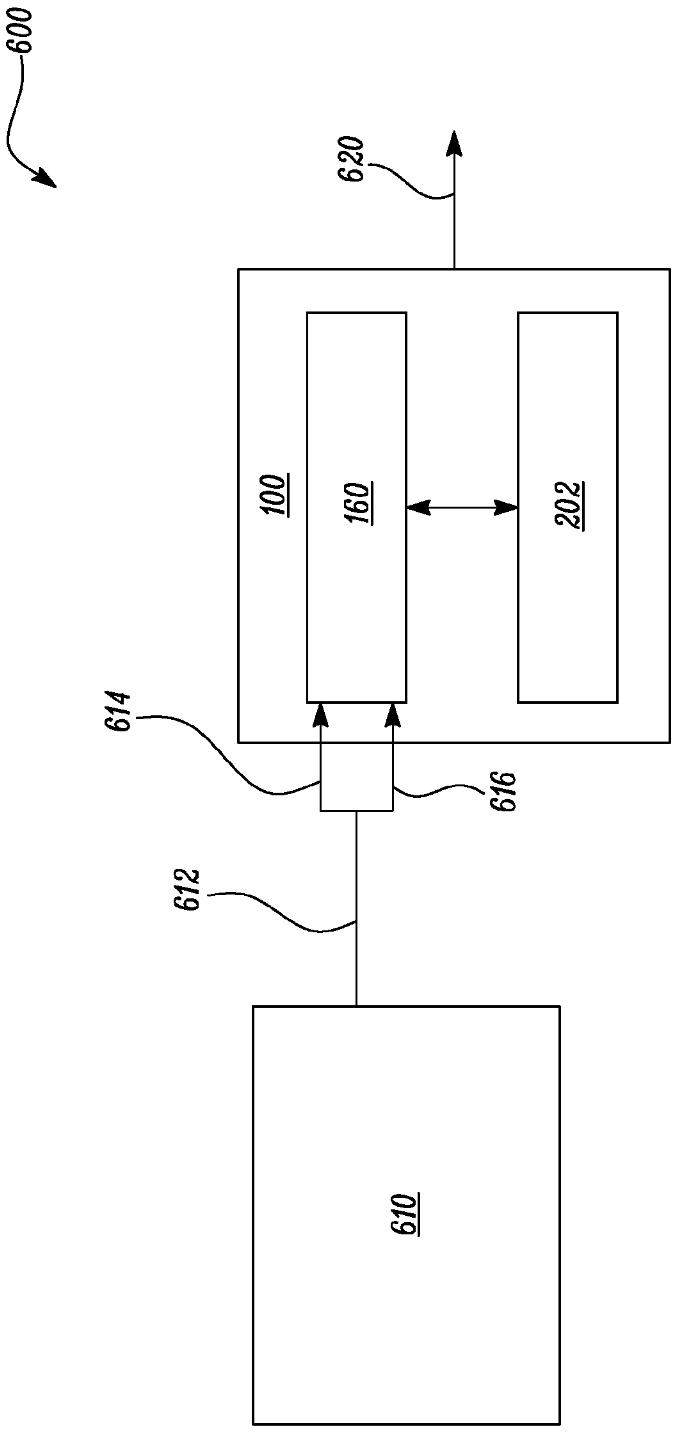
FIG. 6A is a schematic view of an environment including the article of PPE of FIG. 2 and a remotely located article of PPE, according to an embodiment of the present disclosure.

FIG. 6A illustrates a schematic view of the environment 600 including the article 100 and another remotely located article of PPE 610, according to an embodiment of the present disclosure. In some embodiments, the environment 600 may be a location where one or more users of corresponding articles of PPE are deployed. In the illustrated embodiment of FIG. 6, the environment 600 includes the article 100 and the remotely located article of PPE 610. The remotely located article of PPE 610 may be interchangeably referred to as "the article 610".

In some cases, the article 610 may issue an audio alert 612 indicative of an emergency event for the user of the article 610. In such a case, from a point of view of the article 100, the remotely located article 610 has issued a remote audio alert 612 indicative of a remote emergency event for the user of the remotely located article 610. In some embodiments, the detector 160 of the article 100 is configured to receive the remote audio alert 612 indicative of the remote emergency event from the remotely located article 610. Thereafter, the controller 202 is further configured to receive the remote audio alert 612 indicative of the remote emergency event from the remotely located article 610. The controller 202 is further configured to determine a location 620 of the remotely located article 610 relative to the article 100 at least based on an acoustic intensity 614 and a direction 616 of the remote audio alert 612.

In some embodiments, the controller 202 is configured to determine the location 620 of the remotely located article 610 using both the acoustic intensity 614 and the direction 616 of the remote audio alert 612. Specifically, in some embodiments, the controller 202 is configured to determine the location 620 of the remotely located article 610 by determining a sound map 650 (shown in FIG. 6B) of the environment 600.

Figure 6B:
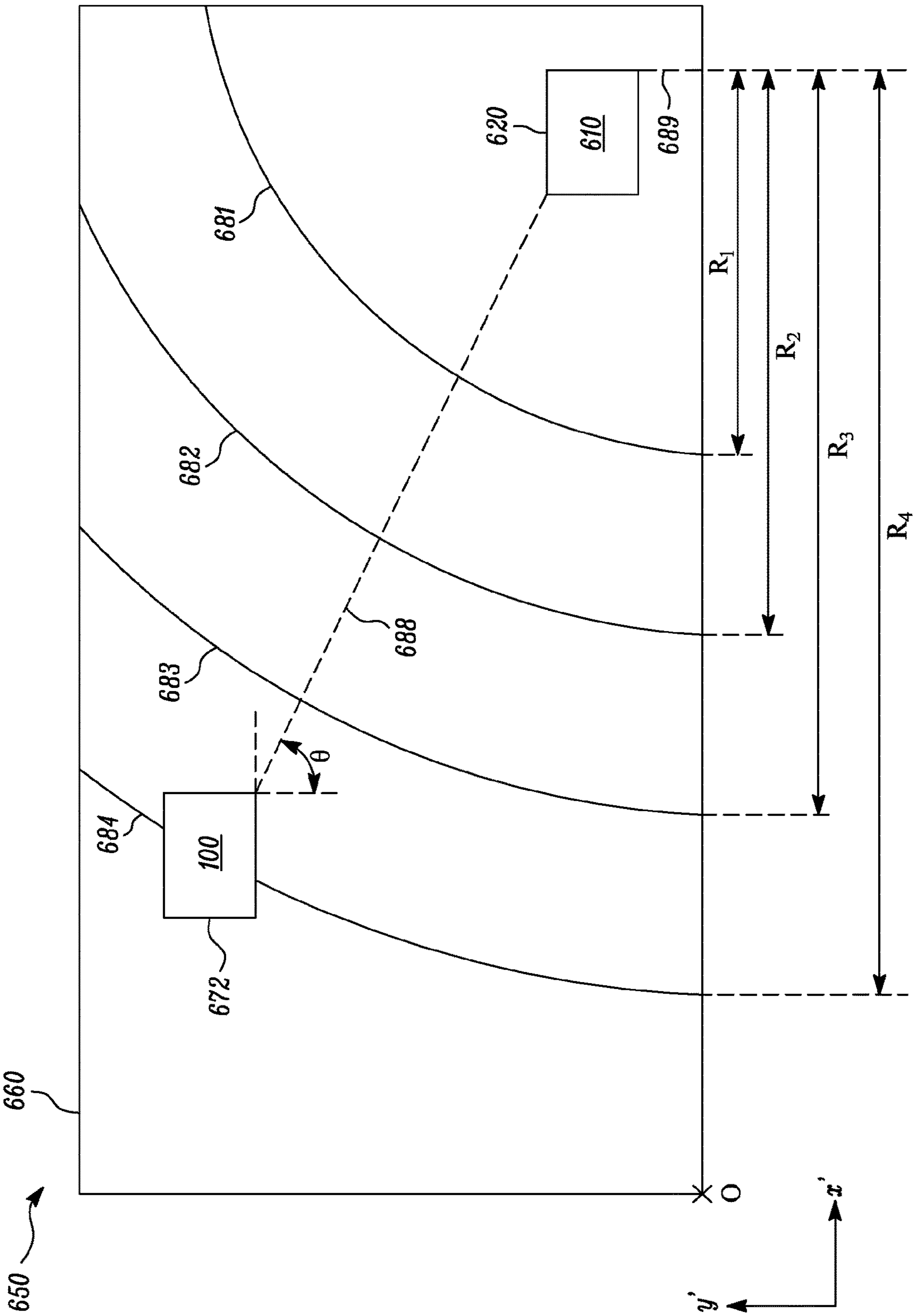
FIG. 6B is a schematic view of a sound map of the environment of FIG. 6A including the article of PPE and the remotely located article of PPE, according to an embodiment of the present disclosure.

FIG. 6B illustrates an example schematic view of the sound map 650 of the environment 600 (shown in FIG. 6A). The sound map 650 includes a floor plan 660 of the environment 600 including the article 100 and the article 610. In some embodiments, the floor plan 660 may be a structural plan of the environment 600 (e.g., a building floor) where the users of the article 100 and the article 610 are present. In some embodiments, the floor plan 660 for the environment 600 may be stored in the fourth dataset 420 of the memory 204 (shown in FIG. 4).

Referring to FIGS. 6A and 6B, in some embodiments, the floor plan 660 may be defined in a cartesian coordinate system, along x' and y'-axes. The article 100 may be at a location 672 having cartesian coordinates (x'1, y'1) with respect to an origin "O".

In some embodiments, the audio alert 612 from the article 610 has a prespecified acoustic intensity at a source of emission of the audio alert 612 (e.g., the article 610). Generally, a sound emitted (e.g. the audio alert 612) from the source radiates from the source radially along a direction of propagation of the sound. With increase in distance from the source, the acoustic intensity of the emitted sound proportionately decreases.

In the illustrated embodiment of FIG. 6B, the audio alert 612 propagates along the x'-axis, and the acoustic intensity of the audio alert 612 decreases with increasing distance along the x'-axis. At radial distances of R1, R2, R3 and R4 from the article 610, the acoustic intensity 614 of the audio alert 612 has respective values 681, 682, 683 and 684 (681-684), such that 684 is less than 683, 683 is less than 682, and 682 is less than 681. The values 681-684 can be calculated and stored in the fourth dataset 420 of the memory 204 (shown in FIG. 4). Based on the acoustic intensity of the audio alert 612 detected by the detector 160 of the article 100, a corresponding distance of the article 610 from the article 100 may be determined. In the illustrated embodiment of FIG. 6B, the detector 160 of the article 100 detects the audio alert 612 having the acoustic intensity 684. Therefore, the controller 202 determines that the article 610 is at a radial distance R4 from the article 610.

Generally, propagation of sound is an anisotropic phenomenon, i.e., sound propagates along a prespecified direction. Specifically, sound has a directionality, i.e., a sound (e.g., the audio alert 612) may propagate at substantially a straight line from a source (e.g., the article 610) of the sound towards a detector (e.g., the detector 160 of the article 100) of the sound. In some embodiments, based on the detected audio alert 612 by the detector 160, the controller 202 determines a direction 616 of the source of the audio alert 612, i.e., the direction 616 at which the article 610 is located. In the illustrated embodiment of FIG. 6B, the article 610 is located at an angle "0" from the article 100 with respect to the y'-axis.

Therefore, based on the angle θ and the radial distance R4 of the article 610 from the article 100, the controller 202 determines the location 620 of the article 610 as a point of intersection of a line 688 from the article 100 at the angle θ with respect to the y-axis and a vertical line 689 at the radial distance R4 from the article 100. In the illustrated embodiment of FIG. 6B, the controller 202 determines the location 620 of the article 610 having cartesian coordinates (x'2, y'2).

Figure 7:
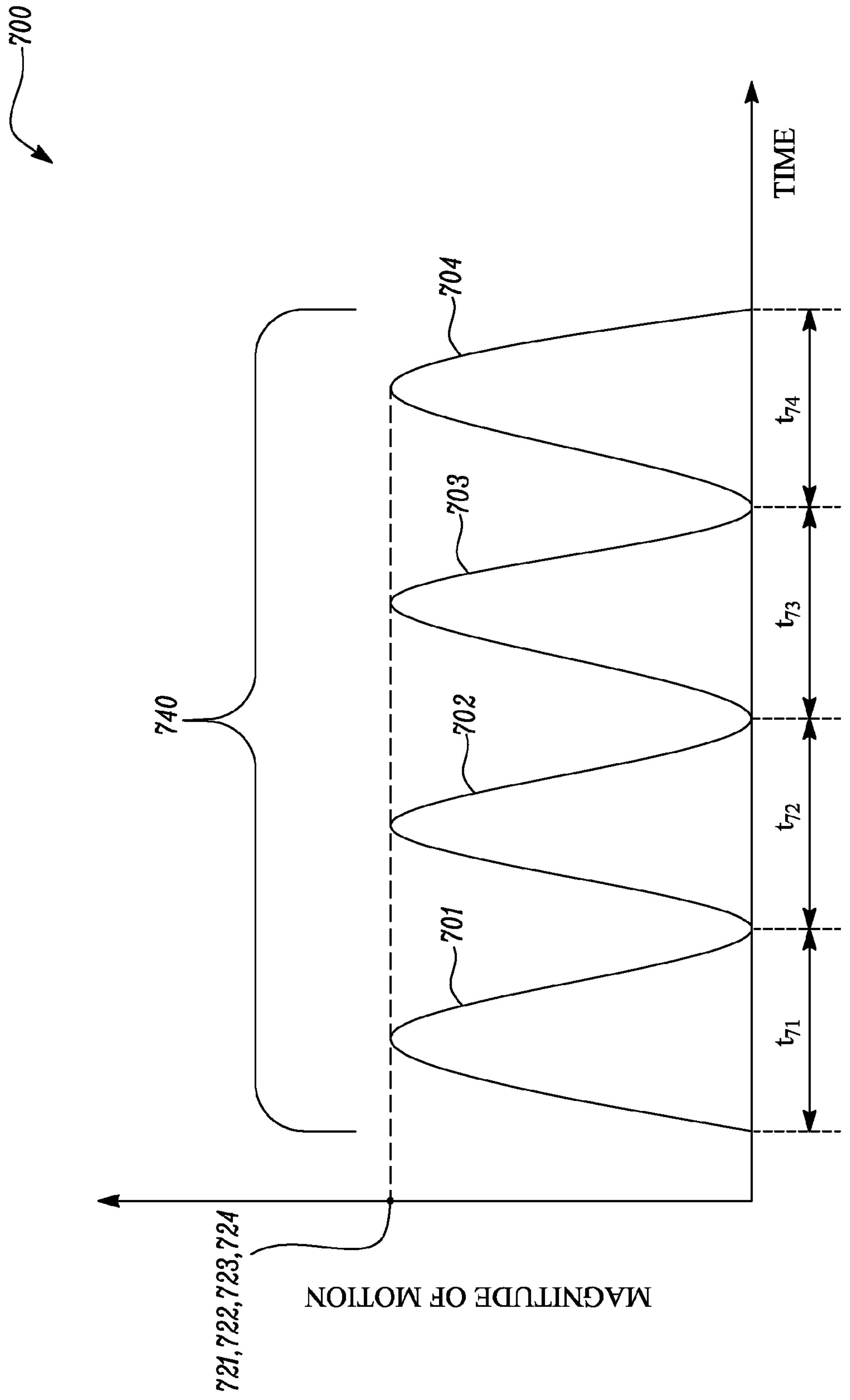
FIG. 7 is a plot of motions of a user of the article of PPE of FIG. 1, according to an embodiment of the present disclosure.

FIG. 7 illustrates a plot 700 of motions of the user of the article 100 (shown in FIG. 2) that are processed by the controller 202, according to an embodiment of the present disclosure. The plot 700 depicts magnitudes of motions on the ordinate axis and time periods on the abscissa. Further, the plot 700 depicts motion along one direction (e.g., the x-axis).

Referring to FIGS. 1, 2, 4 and 7, the plot 700 depicts a plurality of motions 701, 702, 703, 704 occurring over respective time periods t71, t72, t73, t74. The plurality of motions 701, 702, 703, 704 are determined by the controller 202 based on the motion signals 250 received from the at least one sensor 140-1. The plurality of motions 701, 702, 703, 704 have corresponding magnitudes 721, 722, 723, 724. In some embodiments, the controller 202 is configured to determine a motion pattern 740 based on the plurality of motions 701, 702, 703, 704.

In some embodiments, the controller 202 is further configured to determine that the motion pattern 740 includes a plurality of successive repeated motions 701, 702, 703, 704 that are equal to each other with respect to the corresponding magnitudes 721, 722, 723, 724 and corresponding directions. In other words, the controller 202 is configured to determine that the motions pattern 740 includes the successive repeated motions 701, 702, 703, 704, that the successive repeated motions 701, 702, 703, 704 have a same direction (i.e., the x-axis), and that the respective magnitudes 721, 722, 723, 724 of the successive repeated motions 701, 702, 703, 704 are equal to each other.

In some embodiments, the controller 202 is configured to determine the emergency event at least based on the motion pattern 740. Specifically, the controller 202 determines that the emergency event is an emergency medical event upon determining the plurality of successive repeated motions 701, 702, 703, 704. Upon determination of the emergency medical event, the controller 202 generates the alert signal 252 corresponding to the emergency medical event.

For example, the emergency medical event, in which the plurality of successive repeated motions 701, 702, 703, 704 are equal to each other with respect to the corresponding magnitudes 721, 722, 723, 724 and corresponding directions, may be a seizure experienced by the user of the article 100. As the user convulses, the at least one sensor 140-1 may register successive motions substantially along one direction, and having substantially similar magnitudes.

Figure 8:
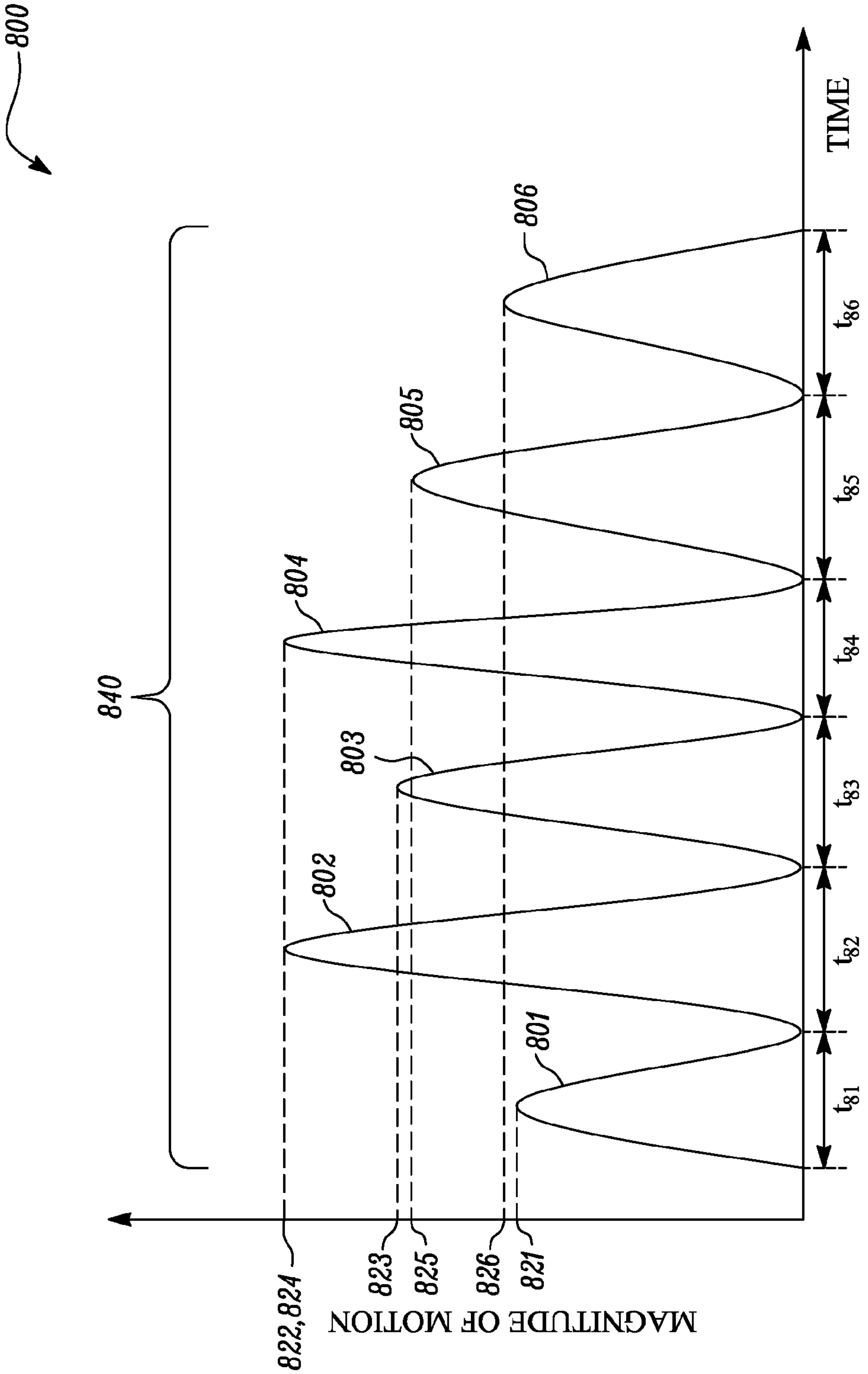
FIG. 8 is a plot of motions of the user of the article of PPE of FIG. 1, according to an embodiment of the present disclosure.

FIG. 8 illustrates another plot 800 of motions of the user of the article 100 that is processed by the controller 202, according to an embodiment of the present disclosure. The plot 800 depicts magnitudes of motions on the ordinate axis, and time periods on the abscissa. Further, the plot 800 depicts motion along one direction (e.g., the x-axis).

Referring to FIGS. 1, 2, 4 and 8, the plot 800 depicts a plurality of motions 801, 802, 803, 804, 805, 806 (801-806). The plurality of motions 801-806 are determined by the controller 202 based on the motion signals 250 received from the at least one sensor 140-1. The plurality of motions 801-806 have corresponding magnitudes 821, 822, 823, 824, 825, 826 (821-826), and occur over respective time periods t81, t82, t83, t83, t84, t85, t86.

In some embodiments, the controller 202 is configured to determine a motion pattern 840 based on the plurality of motions 801-806.

In some embodiments, the controller 202 is further configured to determine that the motion pattern 840 includes a plurality of successive constrained motions 801-806, such that that the corresponding direction of the plurality of successive constrained motions 801-806 are equal to each other, and the corresponding magnitudes of at least two of the plurality of successive constrained motions 801-806 are different from each other. In other words, the controller 202 is configured to determine that the motions pattern 840 includes the successive constrained motions 801-806, that the plurality of successive constrained motions 801-806 have a same direction (i.e., the x-axis), and that the corresponding magnitudes (e.g., 822, 823) of at least two of the successive constrained motions (e.g., 802, 803) are different from each other.

In some embodiments, the controller 202 is configured to determine the emergency event at least based on the motion pattern 840. Specifically, the controller 202 determines that the emergency event is an emergency constraint event upon determining the plurality of successive constrained motions 801-806. Upon determination of the emergency constraint event, the controller 202 generates the alert signal 252 corresponding to the emergency constraint event.

For example, the emergency constraint event, in which the corresponding direction of the plurality of successive constrained motions 801-806 are equal to each other, and the corresponding magnitudes of at least two of the plurality of successive constrained motions 801-806 are different from each other, may occur when the user of the article 100 may be trapped under debris. As the user attempts to escape the entrapment, the at least one sensor 140-1 may register successive constrained motions along one direction, but varying in magnitude.

Figure 9A:
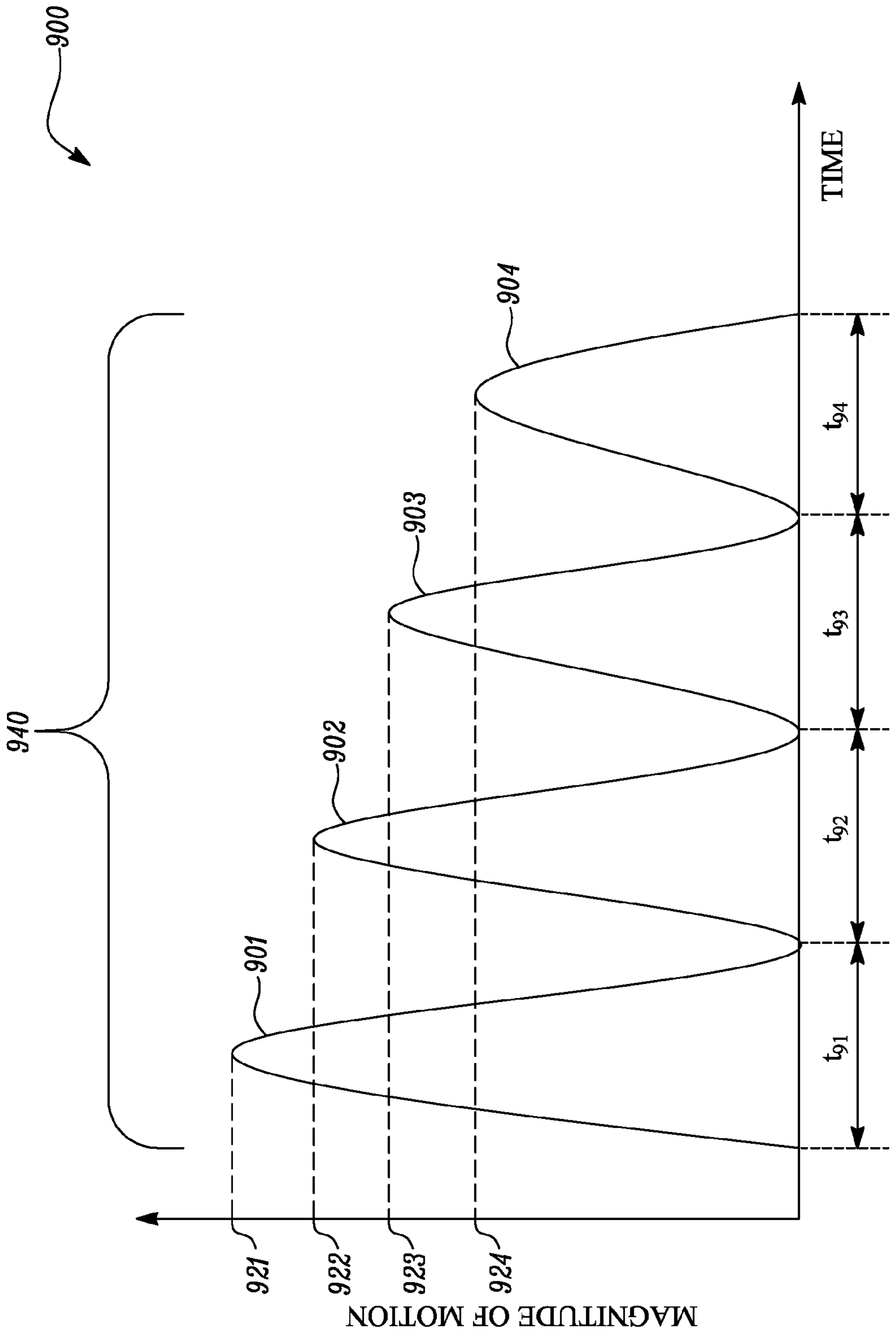
FIG. 9A is a plot of motions of the user of the article of PPE of FIG. 1, according to an embodiment of the present disclosure.

FIG. 9A illustrates another plot 900 of motions of the user of the article 100 that is processed by the controller 202, according to an embodiment of the present disclosure. The plot 900 depicts magnitudes of motions on the ordinate axis, and time periods on the abscissa. Further, the plot 900 depicts motion along one direction (e.g., the x-axis).

Referring to FIGS. 1, 2, 4 and 9A, the plot 900 depicts a plurality of motions 901, 902, 903, 904 (901-904). The plurality of motions 901-904 are determined by the controller 202 based on the motion signals 250 received from the at least one sensor 140-1. The plurality of motions 901-904 have corresponding magnitudes 921, 922, 923, 924 (921-924), and occur over corresponding time periods t91, t92, 93, t94.

In some embodiments, the controller 202 is configured to determine a motion pattern 940 based on the plurality of motions 901-904.

Figure 9B:
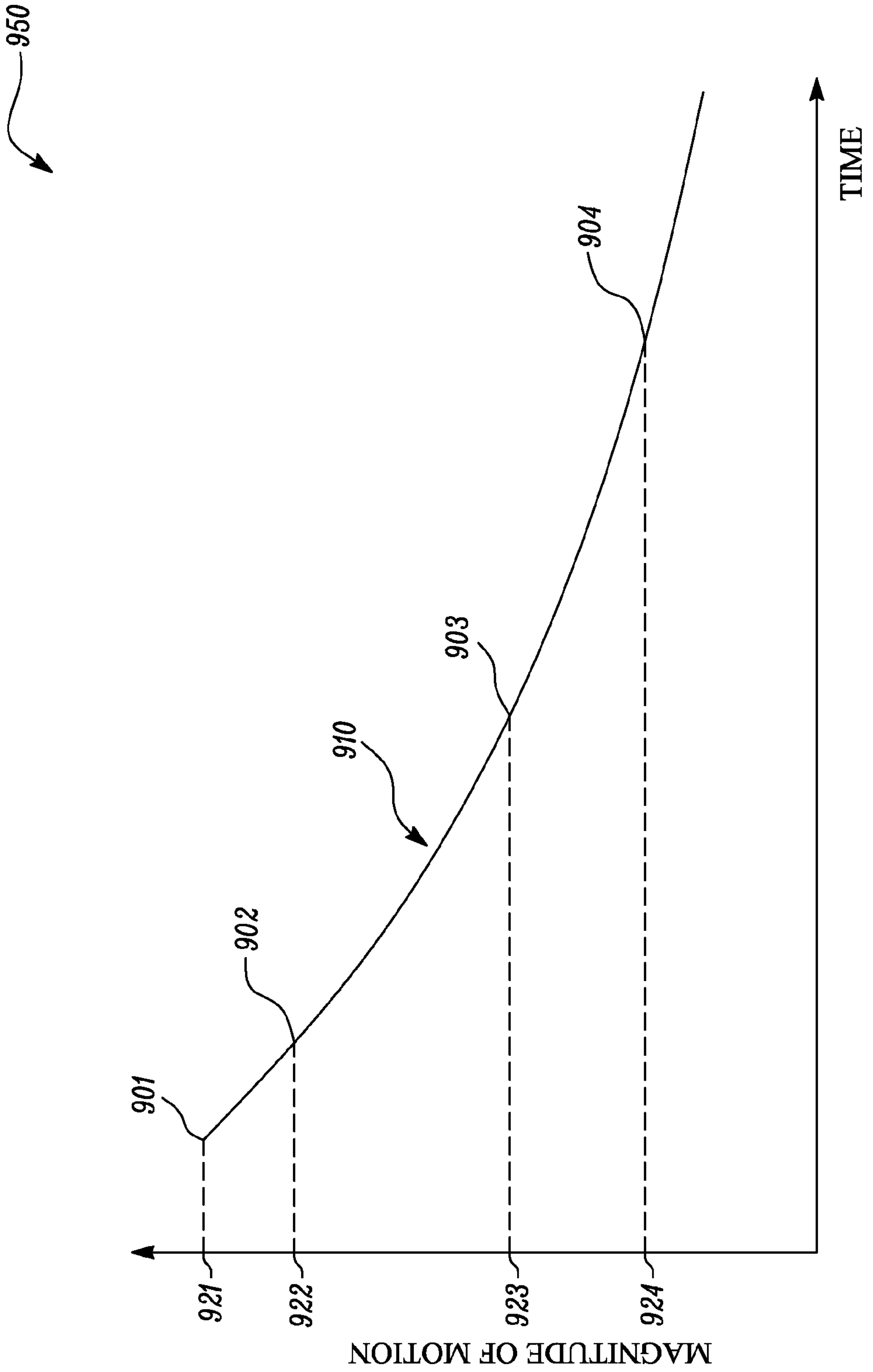
FIG. 9B is a plot of magnitudes of the motions of the user of the article of PPE corresponding to FIG. 9A, according to an embodiment of the present disclosure.

FIG. 9B illustrates a plot 950 of magnitudes of motions of the user of the article 100 corresponding to FIG. 9A The plot 950 depicts magnitudes of motions on the ordinate axis, and time periods on the abscissa.

Referring to FIGS. 1, 2, 4, 9A and 9B, the plot 950 illustrates magnitudes of the plurality of motions 901-904, which are depicted by a motion curve 910. The motion curve 910 depicts a variation of the magnitudes of the plurality of motions 901-904 with time, during a prespecified time period.

In some embodiments, the controller 202 is further configured to determine that the motion pattern 940 includes the plurality of successive constrained motions 901-904, such that that the corresponding direction of the plurality of successive constrained motions 901-904 are equal to each other, and the corresponding magnitudes 921-924 of at least two of the plurality of successive constrained motions 901-904 are different from each other.

The controller 202 determines that the constrained motions 901-904 have the same direction (i.e., the x-axis). Further, the controller 202 determines that the magnitudes 922, 923 of at least two of the successive constrained motions 902, 903 are not equal to each other.

In some embodiments, the controller 202 is further configured to determine the emergency event at least based on the motion pattern 940. Specifically, the controller 202 further determines that the emergency event is the emergency constraint event upon determining that the corresponding magnitudes of the plurality of successive constrained motions 901-904 decrease monotonically with respect to time.

Upon determination of the emergency constraint event, the controller 202 generates the alert signal 252 corresponding to the emergency constraint event.

For example, the emergency constraint event, in which the corresponding magnitudes 921-924 of the plurality of successive constrained motions 901-904 decrease monotonically with respect to time, may occur when the user of the article 100 is trapped under moving debris. As the user attempts to escape the entrapment, the debris may be shifting and may further entrap or constrain the user. Thus, the at least one sensor 140-1 may register successive motions along one direction, but decreasing in magnitude.

Figure 10A:
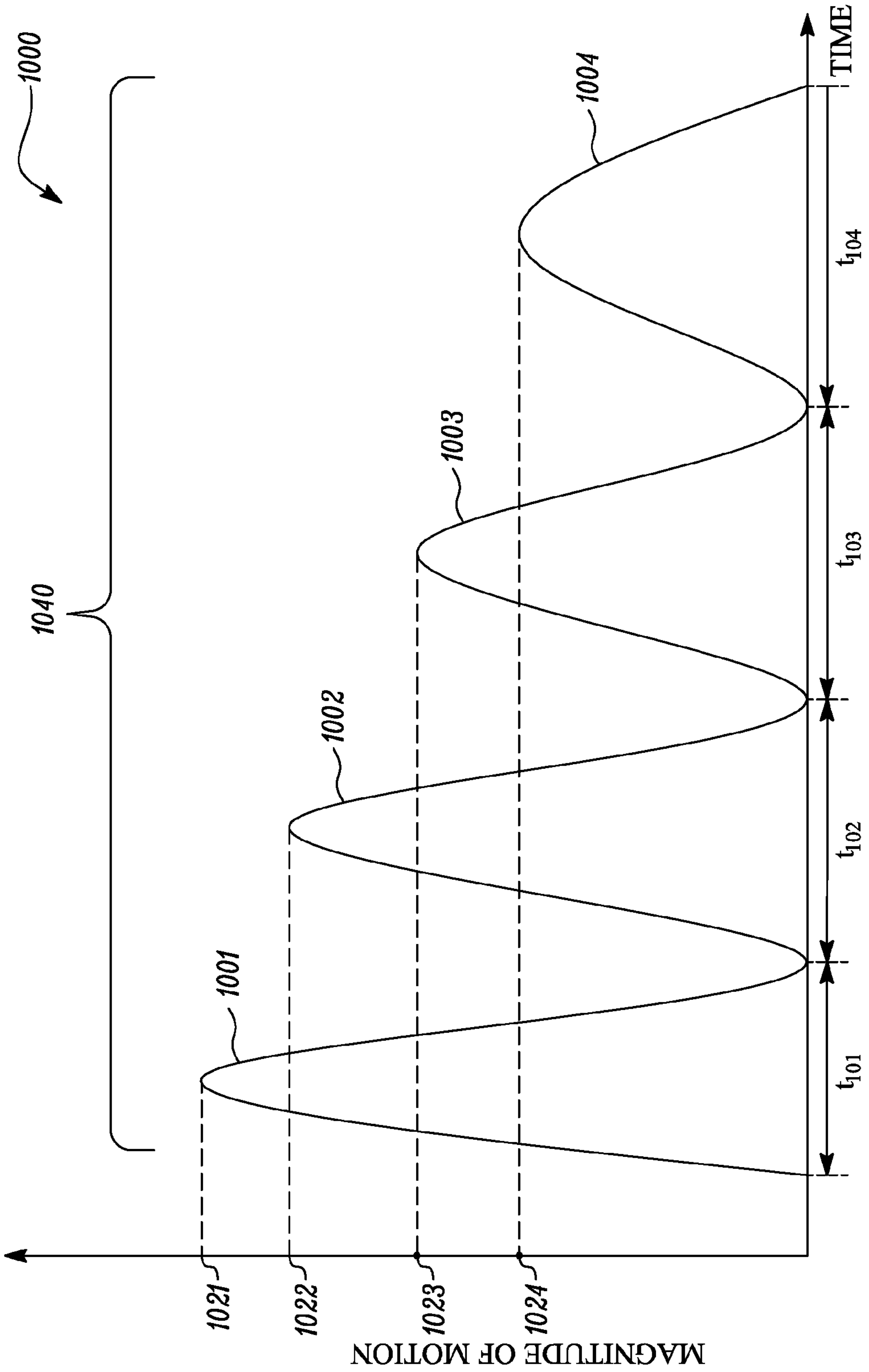
FIG. 10A is a plot of motions of the user of the article of PPE of FIG. 1, according to an embodiment of the present disclosure.

FIG. 10A illustrates another plot 1000 of motions of the user of the article 100 that is processed by the controller, according to an embodiment of the present disclosure. The plot 1000 depicts magnitudes of motions on the ordinate axis and time periods on the abscissa. Further, the plot 1000 depicts motion along one direction (e.g., the x-axis).

Referring to FIGS. 1, 2, 4 and 10A, the plot 1000 depicts a plurality of motions occurring over respective time periods. In the illustrated embodiment of FIG. 10A, the plot 1000 depicts a plurality of motions 1001, 1002, 1003, 1004 (1001-1004) occurring over respective time periods t101, t102, t103, t104. The plurality of motions 1001-1004 are determined by the controller 202 based on the motion signals 250 received from the at least one sensor 140-1. The plurality of motions 1001-1004 have corresponding magnitudes 1021, 1022, 1023, 1024 (1021-1024).

In some embodiments, the controller 202 is configured to determine a motion pattern 1040 based on the plurality of motions 1001-1004.

In some embodiments, the controller 202 is further configured to determine that the motion pattern 1040 includes a plurality of successive constrained motions and that the plurality of successive constrained motions occur over the respective time periods. In the illustrated embodiment of FIG. 10A, the controller 202 is configured to determine that the motion pattern 1040 includes the motions 1001-1004, and is further configured to determine that the constrained motions 1001-1004 occur over the respective time periods t101, t102, t103.

Figure 10B:
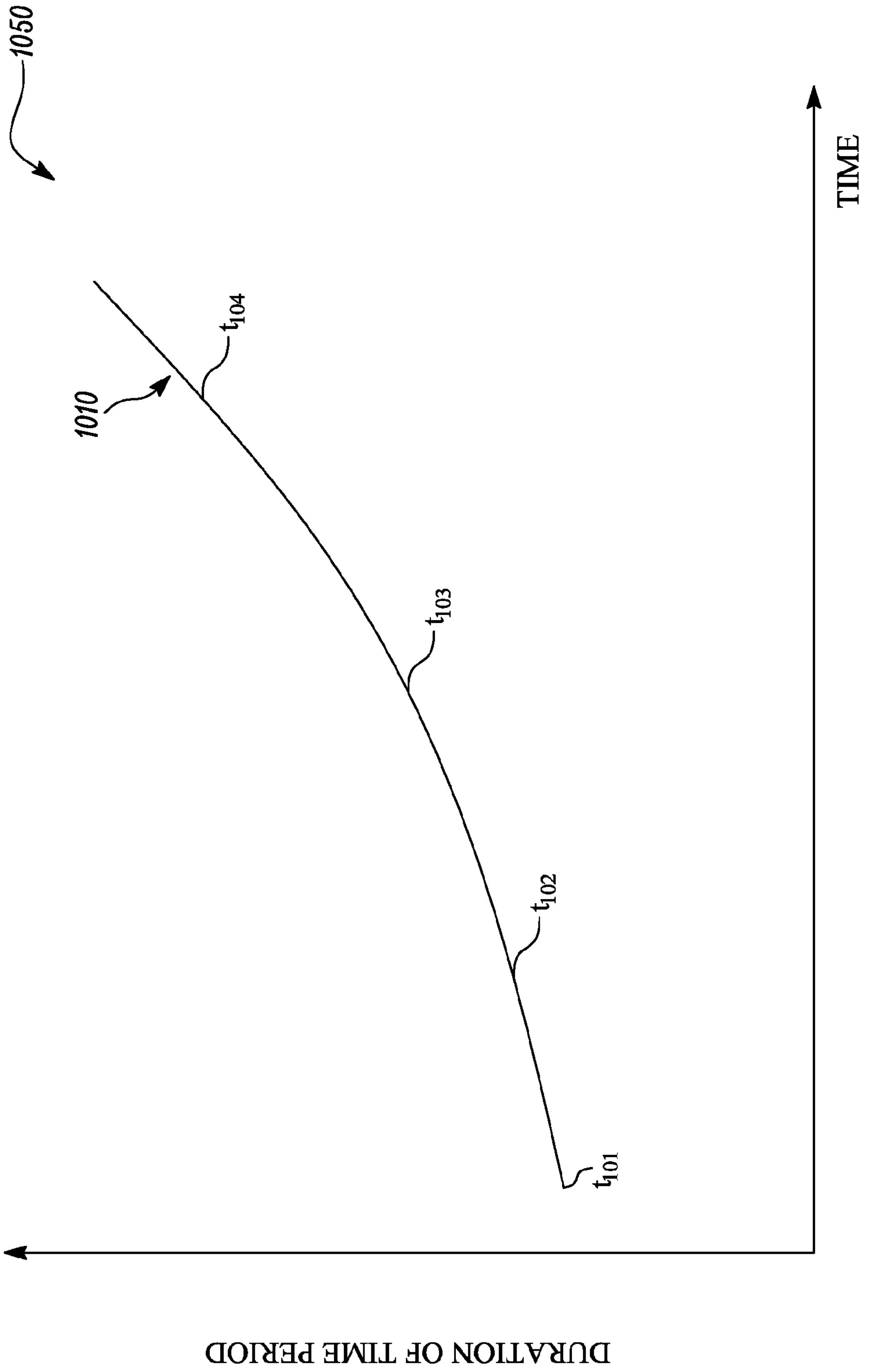
FIG. 10B is a plot of time periods of the motions of the user of article of PPE corresponding to FIG. 10A, according to an embodiment of the present disclosure.

FIG. 10B illustrates a plot 1050 of time periods of motions of the user of the article 100 corresponding to FIG. 10A. The plot 1050 depicts time periods on the abscissa, and a value of duration of the time periods in arbitrary units (a.u.) on the ordinate axis.

Referring to FIGS. 1, 2, 4, 10A and 10B, the plot 1050 illustrates a curve 1010, which depicts a variation in the time periods t101, t102, t103, t104 of the corresponding plurality of motions 1001-1004. The time periods are determined by the controller 202 based on the motion signals 250 received from the at least one sensor 140-1.

In some embodiments, the controller 202 is further configured to determine the emergency event at least based on the motion pattern 1040. Specifically, the controller 202 further determines that the emergency event is the emergency constraint event upon determining that the corresponding time periods t101, t102, t103, t104 of the plurality of successive constrained motions 1001-1004 increase monotonically. In the illustrated embodiment of FIGS. 10A and 10B, the controller 202 determines that the successive constrained motions 1001-1004 occur such that the time periods of each of the successive constrained motions 1001-1004 are different from each other. Specifically, time periods t101, t102, t103, t104 of the corresponding successive constrained motions 1001-1004 increases monotonically. Upon determination of the emergency constraint event, the controller 202 generates the alert signal 252 corresponding to the emergency constraint event.

For example, the emergency constraint event, in which the corresponding time periods t101, t102, t103, t104 of the plurality of successive constrained motions 1001-1004 increase monotonically, may occur when the user of the article 100 is trapped under debris, and experiencing fatigue. As the fatigue increases, the time period of the motion increases. Thus, the at least one sensor 140-1 may register successive motions along one direction, but with increasing time periods.

In some embodiments, the controller 202 may further determine that the corresponding magnitudes of the plurality of successive constrained motions 1001-1004 decrease with respect to time. In other words, the controller 202 determines that magnitudes 1021-1024 decrease with respect to time, i.e., the magnitude 1022 is lesser than the magnitude 1021, the magnitude 1023 is lesser than the magnitude 1022, and the magnitude 1024 is lesser than the magnitude 1023.

For example, the emergency constraint event, in which the corresponding time periods t101, t102, t103, t104 of the plurality of successive constrained motions 1001-1004 increase monotonically and the corresponding magnitudes 1021-1024 of the successive constrained motions 1001-1004 decrease with respect to time, may occur when the user of the article 100 may be losing consciousness. As a result, the magnitude of motion decreases and the time duration of the motion increases. Thus, the at least one sensor 140-1 may register successive motions along one direction, but decreasing in magnitude and with increasing time periods.

Figure 11:
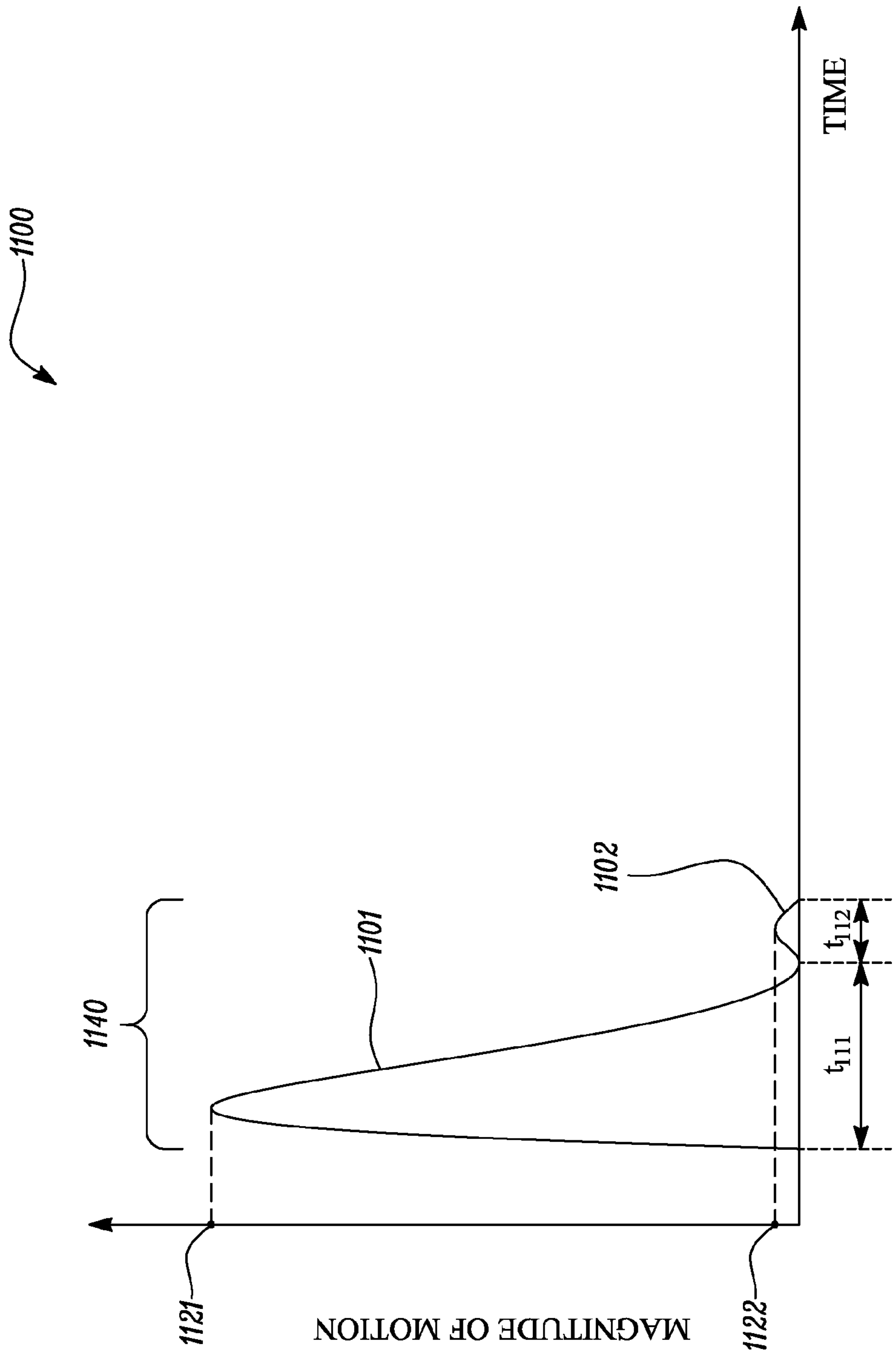
FIG. 11 is a plot of motions of the user of the article of PPE of FIG. 1, according to an embodiment of the present disclosure.

FIG. 11 illustrates another plot 1100 of motions of the user of the article 100 that is processed by the controller 202, according to an embodiment of the present disclosure. The plot 1100 depicts magnitudes of motions on the ordinate axis, and time periods on the abscissa. Further, the plot 1100 depicts motion along one direction (e.g., the x-axis).

Referring to FIGS. 1, 2, 4 and 11, the plot 1100 depicts a plurality of motions 1101, 1102 occurring over corresponding time periods t111, t112. The plurality of motions 1101, 1102 are determined by the controller 202 based on the motion signals 250 received from the at least one sensor 140-1. The plurality of motions 1101, 1102 have corresponding magnitudes 1121, 1122. In some embodiments, the controller 202 is configured to determine a motion pattern 1140 based on the plurality of motions 1101, 1102. The plurality of motions 1101, 1102 are interchangeably referred to as a first motion 1101 and a second motion 1102. The first and second motions 1101, 1102 occur successively, over time periods t111, t112, respectively.

In some embodiments, the controller 202 is further configured to determine that the motion pattern 1140 includes the first motion 1101 and the second motion 1102 succeeding the first motion 1101, such that a ratio of the magnitude 1121 of the first motion 1101 to the magnitude 1122 of the second motion 1102 is greater than or equal to 100. In other words, the controller 202 is further configured to determine that the magnitude 1121 of the first motion 1101 is substantially greater than the magnitude 1122 of the second motion 1102.

In some embodiments, the controller 202 is configured to determine the emergency event at least based on the motion pattern 1140. Specifically, the controller 202 determines that the emergency event is at least one of a fall event and a collapse event upon determining that the motion pattern 1140 includes the first motion 1101 and the second motion 1102. Upon determination of the at least one of the fall event and the collapse event, the controller 202 generates the alert signal 252 corresponding to the emergency medical event.

In some examples, the emergency event, in which ratio of the magnitude 1121 of the first motion 1101 to the magnitude 1122 of the second motion 1102 is greater than or equal to 100, may be the fall event, when the user of the article 100 falls. The at least one sensor 140-1 may register a single motion, followed by a period of negligible or no motion.

In some other examples, the emergency event, in which ratio of the magnitude 1121 of the first motion 1101 to the magnitude 1122 of the second motion 1102 is greater than or equal to 100, may be a collapse event, when the user of the article 100 collapses due to an acute bout of unconsciousness. In such cases, the at least one sensor 140-1 may register a single motion, followed by a period of negligible or no motion.

Figure 12:
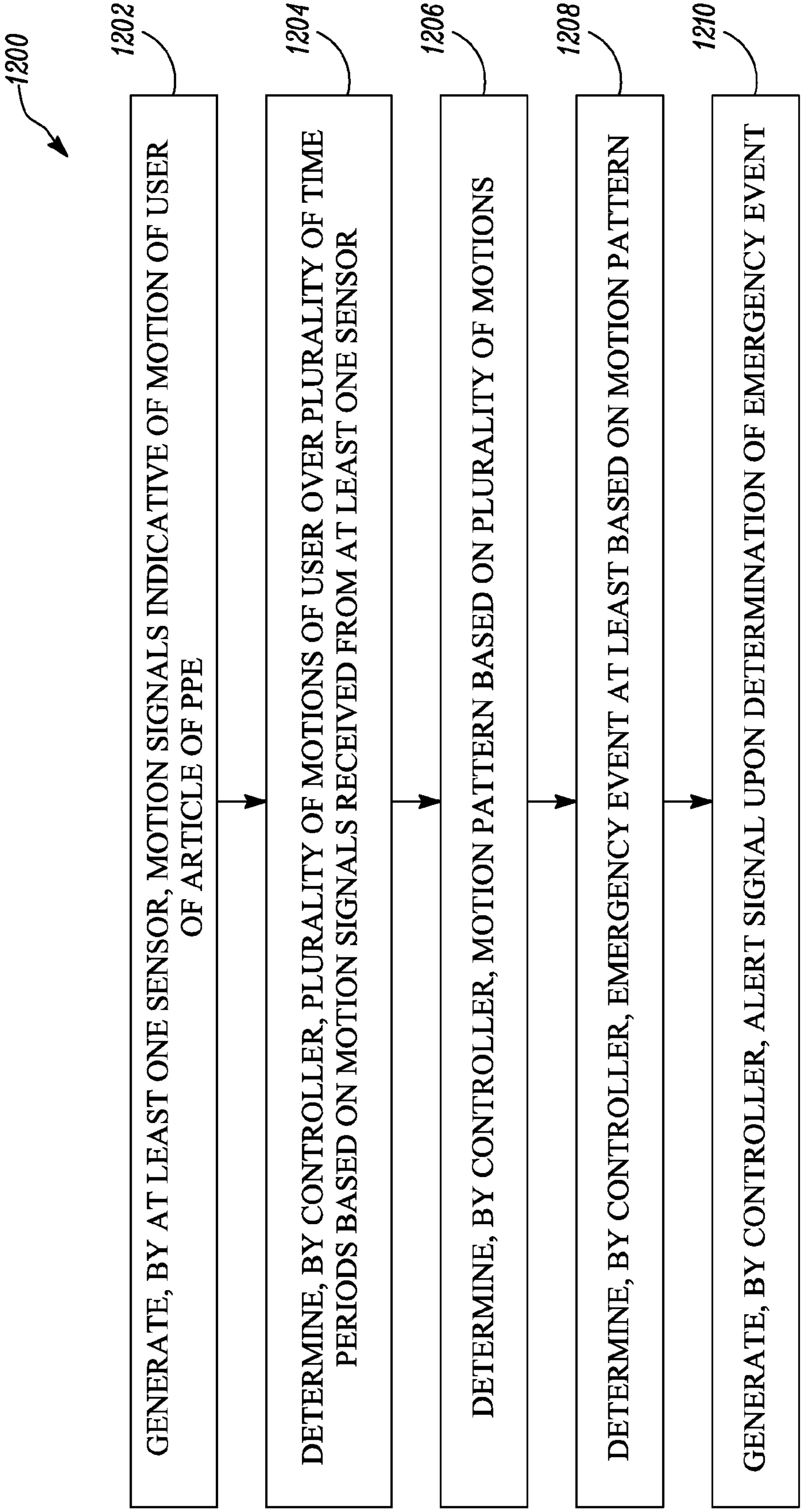
FIG. 12 is a flowchart depicting a method for use with the article of PPE of FIG. 2, according to an embodiment of the present disclosure.

FIG. 12 illustrates a flowchart depicting a method 1200 for use with the article 100 according to an embodiment of the present disclosure.

Referring to FIGS. 1, 2 and 12, at step 1202, the method 1200 includes generating, by the at least one sensor 140-1, motion signals 250 indicative of a motion of a user of the article 100. At step 1204, the method 1200 includes determining, by the controller 202, the plurality of motions over the plurality of time periods based on the motion signals 250 received from the at least one sensor 140-1. In some embodiments, each motion from the plurality of motions occurs over a corresponding time period from the plurality of time periods. In some embodiments, each motion includes a corresponding magnitude and a corresponding direction over the corresponding time period.

At step 1206, the method 1200 includes determining, by the controller 202, the motion pattern based on the plurality of motions, such that the motion pattern includes the at least one motion from the plurality of motions that has a non-zero value for the corresponding magnitude.

At step 1208, the method 1200 includes determining, by the controller 202, the emergency event at least based on the motion pattern. At step 1210, the method 1200 includes generating, by the controller 202, the alert signal 252 upon determination of the emergency event. In some embodiments, the method 1200 further includes generating, by the alarm circuit 208, the alert 254 upon receiving the alert signal 252 from the controller 202.

In some embodiments, determining the emergency event further includes comparing the motion pattern with a plurality of motion signatures stored in the memory 204.

Referring now to FIGS. 1, 2, 5B and 12, in some embodiments, the method 1200 further includes controlling, by the visual alarm circuit 522, at least one optical parameter of each of the plurality of light sources 524 based on the alert signal 252 received from the controller 202 in order to generate the visual alert 530. In some embodiments, the method 1200 further includes embedding the information 256 in the visual alert 530.

Referring now to FIGS. 1, 2, 6 and 12, in some embodiments, the method 1200 further includes receiving, by the controller 202, the remote audio alert 612 indicative of the remote emergency event from the other remotely located article 610. In some embodiments, the method 1200 further includes determining the location 620 of the remotely located article 610 at least based on the acoustic intensity 614 and the direction 616 of the remote audio alert 612.

Referring now to FIGS. 1, 2, 7 and 12, in some embodiments, the method 1200 further includes determining that the motion pattern 740 includes the plurality of successive repeated motions 701, 702, 703, 704 that are equal to each other with respect to the corresponding magnitudes 721, 722, 723, 724 and corresponding directions. In some embodiments, the method 1200 further includes determining that the emergency event is the emergency medical event upon determining the plurality of successive repeated motions 701, 702, 703, 704.

Referring now to FIGS. 1, 2, 8 and 12, in some embodiments, the method 1200 further includes determining that the motion pattern 840 includes the plurality of successive constrained motions 841, 842, 843, such that that the corresponding direction of the plurality of successive constrained motions 841, 842, 843 are equal to each other, and the corresponding magnitudes of at least two of the plurality of successive constrained motions 841, 842, 843 are different from each other. In some embodiments, the method 1200 further includes determining that the emergency event is the emergency constraint event upon determining the plurality of successive constrained motions 841, 842, 843.

Referring now to FIGS. 1, 2, 9 and 12, in some embodiments, the method 1200 includes determining that the emergency event is the emergency constraint event upon determining that the corresponding magnitudes of the plurality of successive constrained motions 941, 942, 943 decrease monotonically with respect to time.

Referring now to FIGS. 1, 2, 10 and 12, in some embodiments, the method 1200 includes determining that the emergency event is the emergency constraint event upon determining that the corresponding time periods of the plurality of successive constrained motions 1041, 1042, 1043 increase monotonically.

Referring now to FIGS. 1, 2, 11 and 12, in some embodiments, the method 1200 includes determining that the motion pattern 1140 includes the first motion 1101 and the second motion 1102 succeeding the first motion 1101, such that the ratio of the magnitude 1121 of the first motion 1101 to the magnitude 1122 of the second motion 1102 is greater than or equal to 100. In some embodiments, the method 1200 further includes determining that the emergency event is at least one of a fall event and a collapse event upon determining that the motion pattern 1140 includes the first motion 1101 and the second motion 1102.

The article of PPE 100 of the present disclosure may analyze the motion of the user to determine motion patterns that may be indicative of emergency events for the user, such as medical conditions, entrapment, fall etc. Specifically, the article of PPE 100 may determine emergency events for the user even though the user is in motion. The article of PPE 100 may receive the motion signals 250 from at least one sensor 140-1, such as an accelerometer that is provided on the user, and analyze the motion signals 250 to determine a motion of the user over a period of time. The motion signals 250 may include the magnitude and the direction of the motion. The article of PPE 100 may determine the motion pattern from the motions of the user. The article of PPE 100 may further be provided with the dataset of motion signatures (e.g., first dataset 402) corresponding to various emergency events for the user. On comparison of the determined motion pattern with the dataset, the emergency event for the user may be determined.

The article of PPE 100 of the present disclosure may further include the plurality of light sources 524. When the PASS device 150 registers the emergency event, the visual alert 530 may be generated and transmitted through the plurality of light sources 524, in addition to the audio alert 510. The visual alert 530 may further broadcast the health or state of the user. In some cases, the visual alert 530, as well as the audio alert 510, may carry the embedded information 256, such as the identity of the user or the nature of the emergency event.

The article of PPE 100 of the present disclosure may be provided with the detector 160 to detect the remote audio alert 612 generated by another article of PPE 610 associated with another user in the same environment 600. The article of PPE 100 may determine the location 620 of the other article of PPE 610 based on the acoustic intensity 614 and the direction 616 of the remote audio alert 612.

Further, the article of PPE 100 may be provided with the model 410 including a machine learning and an artificial intelligence to determine the emergency event.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. An article of personal protective equipment (PPE), comprising:

at least one sensor configured to generate motion signals indicative of a motion of a user of the article of PPE; and a controller communicably coupled to the at least one sensor, wherein the controller is configured to:

determine a plurality of motions of the user over a plurality of time periods based on the motion signals received from the at least one sensor, wherein each motion from the plurality of motions occurs over a corresponding time period from the plurality of time periods, and wherein each motion comprises a corresponding magnitude and a corresponding direction over the corresponding time period;

determine a motion pattern based on the plurality of motions, such that the motion pattern comprises at least one motion from the plurality of motions that has a non-zero value for the corresponding magnitude;

determine that the motion pattern comprises a plurality of successive constrained motions, such that the corresponding directions of the plurality of successive constrained motions are equal to each other and corresponding magnitudes of at least two of the plurality of successive constrained motions are different from each other;

determine an emergency event corresponding to the health or state of the user in a hazardous environment at least based on the motion pattern;

determine that the emergency event is an emergency constraint event upon determining the plurality of successive constrained motions; and generate an alert signal upon determination of the emergency event.

2. The article of PPE of claim 1, wherein the controller is further configured to:

determine that the motion pattern comprises a plurality of successive repeated motions that are equal to each other with respect to the corresponding magnitudes and corresponding directions; and determine that the emergency event is an emergency medical event upon determining the plurality of successive repeated motions.

3. The article of PPE of claim 1, wherein the controller is further configured to determine that the emergency event is the emergency constraint event upon determining that the corresponding magnitudes of the plurality of successive constrained motions decrease monotonically with respect to time.

4. The article of PPE of claim 1, wherein the controller is further configured to determine that the emergency event is the emergency constraint event upon determining that the corresponding time periods of the plurality of successive constrained motions increase monotonically.

5. The article of PPE of claim 1, wherein the controller is further configured to:

determine that the motion pattern comprises a first motion and a second motion succeeding the first motion, such that a ratio of the magnitude of the first motion to the magnitude of the second motion is greater than or equal to 100; and determine that the emergency event is at least one of a fall event, and a collapse event upon determining that the motion pattern comprises the first motion and the second motion.

6. The article of PPE of claim 1, further comprising a personal alert safety system (PASS) device communicably coupled to the at least one sensor, wherein the PASS comprises the controller.

7. The article of PPE of claim 1, wherein the at least one sensor comprises at least one of an accelerometer, and a gyroscope.

8. The article of PPE of claim 1, further comprising an alarm circuit communicably coupled to the controller, wherein the alarm circuit is configured to generate an alert upon receiving the alert signal from the controller.

9. The article of PPE of claim 8, wherein the alert comprises an information indicative of at least one of an identification of the user of the article of PPE and a type of the emergency event.

10. The article of PPE of claim 8, wherein the alert comprises at least one of an audio alert, a visual alert, a haptic alert, and a notification.

11. The article of PPE of claim 1, further comprising a memory communicably coupled to the controller, wherein the memory stores a plurality of motion signatures, and wherein the controller is configured to determine the emergency event further based on a comparison between the motion pattern and the plurality of motion signatures.

12. The article of PPE of claim 1, further comprising:

a plurality of light sources configured to emit light; and a visual alarm circuit communicably coupled to the plurality of light sources and the controller, wherein the visual alarm circuit is configured to receive the alert signal from the controller and control at least one optical parameter of each of the plurality of light sources based on the alert signal in order to generate a visual alert, and wherein the visual alert comprises an information indicative of at least one of an identification of the user of the article of PPE and a type of the emergency event.

13. The article of PPE of claim 12, wherein the at least one optical parameter comprises one or more of a flicker rate, an optical intensity, a wavelength, and a switching pattern of the plurality of light sources.

14. The article of PPE of claim 12, wherein the controller is further configured to:

receive a remote audio alert indicative of a remote emergency event from another remotely located article of PPE; and determine a location of the remotely located article of PPE relative to the article of PPE at least based on an acoustic intensity and a direction of the remote audio alert.

15. A method for use with an article of personal protective equipment (PPE) comprising at least one sensor and a controller, the method comprising:

generating, by the at least one sensor, motion signals indicative of a motion of a user of the article of PPE;

determining, by the controller, a plurality of motions of the user over a plurality of time periods based on the motion signals received from the at least one sensor, wherein each motion from the plurality of motions occurs over a corresponding time period from the plurality of time periods, and wherein each motion comprises a corresponding magnitude and a corresponding direction over the corresponding time period;

determining, by the controller, a motion pattern based on the plurality of motions, such that the motion pattern comprises at least one motion from the plurality of motions that has a non-zero value for the corresponding magnitude;

determining that the motion pattern comprises a plurality of successive constrained motions, such that the corresponding directions of the plurality of successive constrained motions are equal to each other and corresponding magnitudes of at least two of the plurality of successive constrained motions are different from each other;

determining, by the controller, an emergency event corresponding to the health or state of the user in a hazardous environment at least based on the motion pattern, and determining that the emergency event is an emergency constraint event upon determining the plurality of successive constrained motions; and generating, by the controller, an alert signal upon determination of the emergency event.

16. The method of claim 15, further comprising:

determining that the motion pattern comprises a plurality of successive repeated motions that are equal to each other with respect to the corresponding magnitudes and corresponding directions; and determining that the emergency event is an emergency medical event upon determining the plurality of successive repeated motions.

17. The method of claim 15, wherein determining that the emergency event is the emergency constraint event further comprises determining that the corresponding magnitudes of the plurality of successive constrained motions decrease monotonically with respect to time.

18. The method of claim 15, wherein determining that the emergency event is the emergency constraint event further comprises determining that the corresponding time periods of the plurality of successive constrained motions increase monotonically.

19. An article of personal protective equipment (PPE), comprising:

at least one sensor configured to generate motion signals indicative of a motion of a user of the article of PPE; and a plurality of light sources configured to emit light;

a controller communicably coupled to the at least one sensor, wherein the controller is configured to:

determine a plurality of motions of the user over a plurality of time periods based on the motion signals received from the at least one sensor, wherein each motion from the plurality of motions occurs over a corresponding time period from the plurality of time periods, and wherein each motion comprises a corresponding magnitude and a corresponding direction over the corresponding time period;

determine a motion pattern based on the plurality of motions, such that the motion pattern comprises at least one motion from the plurality of motions that has a non-zero value for the corresponding magnitude;

determine an emergency event corresponding to the health or state of the user in a hazardous environment at least based on the motion pattern; and generate an alert signal upon determination of the emergency event; and a visual alarm circuit communicably coupled to the plurality of light sources and the controller, wherein the visual alarm circuit is configured to receive the alert signal from the controller and control at least one optical parameter of each of the plurality of light sources based on the alert signal in order to generate a visual alert, and wherein the visual alert comprises an information indicative of at least one of an identification of the user of the article of PPE and a type of the emergency event.

* * * * *